United States Patent
Qi et al.

(10) Patent No.: US 12,318,232 B2
(45) Date of Patent: Jun. 3, 2025

(54) PET RECONSTRUCTION FOR ADJUSTABLE PET SYSTEM

(71) Applicant: CANON MEDICAL SYSTEMS CORPORATION, Tochigi (JP)

(72) Inventors: Wenyuan Qi, Vernon Hills, IL (US); Kent C. Burr, Vernon Hills, IL (US); Yi Qiang, Vernon Hills, IL (US); Evren Asma, Vernon Hills, IL (US); Jeffrey Kolthammer, Vernon Hills, IL (US)

(73) Assignee: CANON MEDICAL SYSTEMS CORPORATION, Tochigi (JP)

( * ) Notice: Subject to any disclaimer, the term of this patent is extended or adjusted under 35 U.S.C. 154(b) by 291 days.

(21) Appl. No.: 17/963,737

(22) Filed: Oct. 11, 2022

(65) Prior Publication Data

US 2024/0122558 A1 Apr. 18, 2024

(51) Int. Cl.
*A61B 6/03* (2006.01)
*A61B 6/00* (2024.01)
(Continued)

(52) U.S. Cl.
CPC ............ *A61B 6/037* (2013.01); *A61B 6/4258* (2013.01); *A61B 6/54* (2013.01); *G01T 1/1641* (2013.01); *G01T 1/2985* (2013.01); *A61B 6/481* (2013.01)

(58) Field of Classification Search
CPC ......... A61B 6/037; A61B 6/4258; A61B 6/54; A61B 6/481; A61B 6/4266; G01T 1/2985; G01T 1/1641
See application file for complete search history.

(56) References Cited

U.S. PATENT DOCUMENTS 5,591,977 A   1/1997  Green et al.
5,825,031 A  10/1998  Wong et al.
(Continued)

FOREIGN PATENT DOCUMENTS

CA   2786368 A1 *  2/2014  ............. A61B 6/481

OTHER PUBLICATIONS

Robert L. Siddon, "Fast calculation of the exact radiological path for a three-dimensional CT array", Medical Physics, vol. 12, No. 2, Mar.-Apr. 1985, pp. 252-255.
(Continued)

*Primary Examiner* — Dani Fox
*Assistant Examiner* — Casey Bryant
(74) *Attorney, Agent, or Firm* — Oblon, McClelland, Maier & Neustadt, L.L.P.

(57) ABSTRACT

A PET scanner includes gamma-ray detector rings that form a bore through which an imaging subject is translated, a length of the bore defining an axial length of the PET scanner, the gamma-ray detector rings being movable along the axial length, the gamma-ray detector rings including gamma-ray detector modules therein, and processing circuitry configured to receive PET data associated with a plurality of transaxial slices of the imaging subject, the PET data including a first set of spatial information and timing information corresponding to a first data acquisition period for the gamma-ray detector modules in a first axial position and a second set of spatial information and timing information corresponding to a second data acquisition period for the gamma-ray detector modules in a second axial position, and reconstruct a PET image based on the first set of spatial and timing information and the second set of spatial and timing information.

12 Claims, 17 Drawing Sheets

(51) Int. Cl.
*A61B 6/42* (2024.01)
*G01T 1/164* (2006.01)
*G01T 1/29* (2006.01)

(56) References Cited

U.S. PATENT DOCUMENTS

| | | | |
|---|---|---|---|
| 6,184,530 B1 | 2/2001 | Hines et al. | |
| 7,262,415 B2 | 8/2007 | Crosetto | |
| 8,558,181 B2 | 10/2013 | Gagnon et al. | |
| 8,594,404 B2 * | 11/2013 | Yamaya | G01T 1/1603 |
| | | | 250/363.04 |
| 11,096,633 B1 * | 8/2021 | Qi | A61B 6/483 |
| 2013/0087697 A1 | 4/2013 | Xie et al. | |
| 2016/0183893 A1 | 6/2016 | Zhang et al. | |
| 2017/0039738 A1 * | 2/2017 | Ziv | G01T 1/249 |
| 2020/0345322 A1 | 11/2020 | Bai et al. | |
| 2022/0022834 A1 | 1/2022 | Nehmeh et al. | |
| 2022/0113437 A1 | 4/2022 | Qi et al. | |
| 2024/0122558 A1 * | 4/2024 | Qi | A61B 6/037 |

OTHER PUBLICATIONS

G. Han, et al., "A fast ray-tracing technique for TCT and ECT studies", IEEE Nuclear Science Symposium, Conference Record, Nuclear Science Symposium and Medical Imaging Conference (Cat. No. 99CH37019), Oct. 24-30, 1999, pp. 1515-1518 (Abstract only).

Wenyuan Qi, et al., "Limited-angle effect compensation for respiratory binned cardiac SPECT," Medical Physics, vol. 43, No. 1, Jan. 2016, pp. 443-454.

Sara Zein, et al., "Performance evaluation of a sparse detector rings PET scanner with extended axial field of view", Journal of Nuclear Medicine (JMN), vol. 60, Issue Supplement 1, May 2019, 5 pages (Abstract only).

* cited by examiner

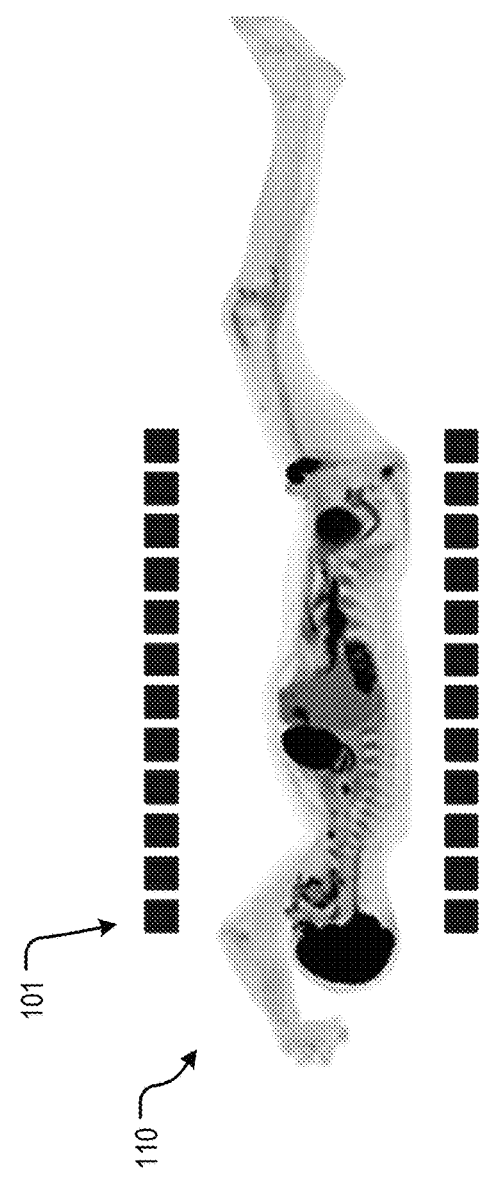
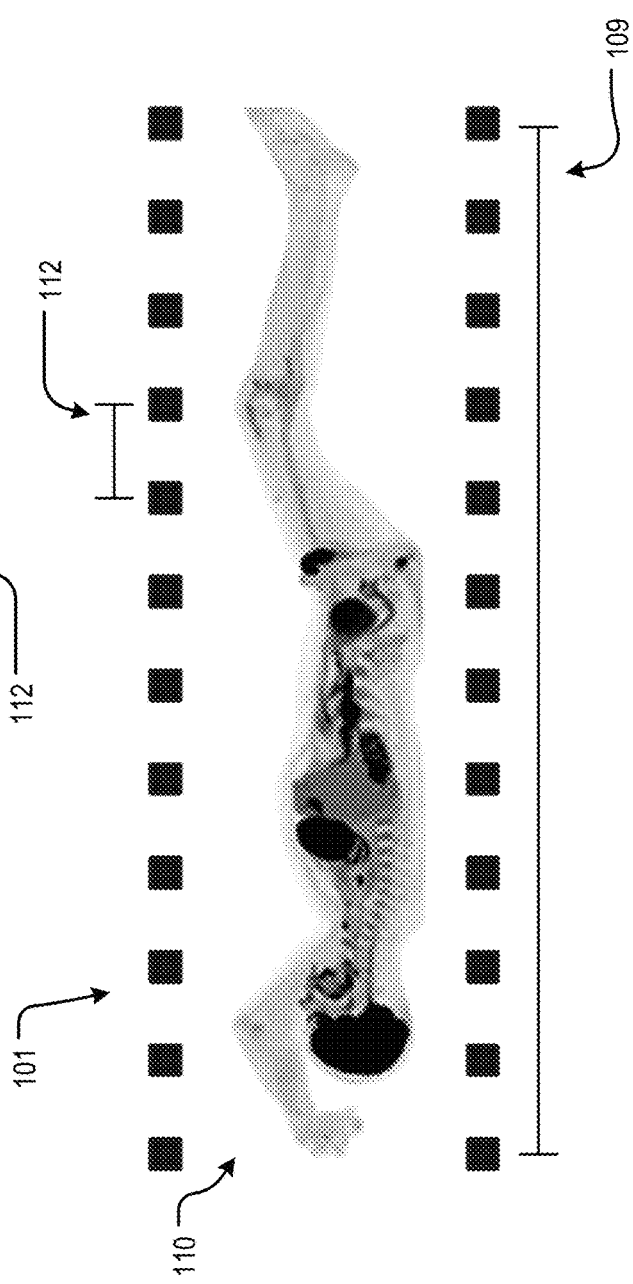
FIG. 1A
FIG. 1B

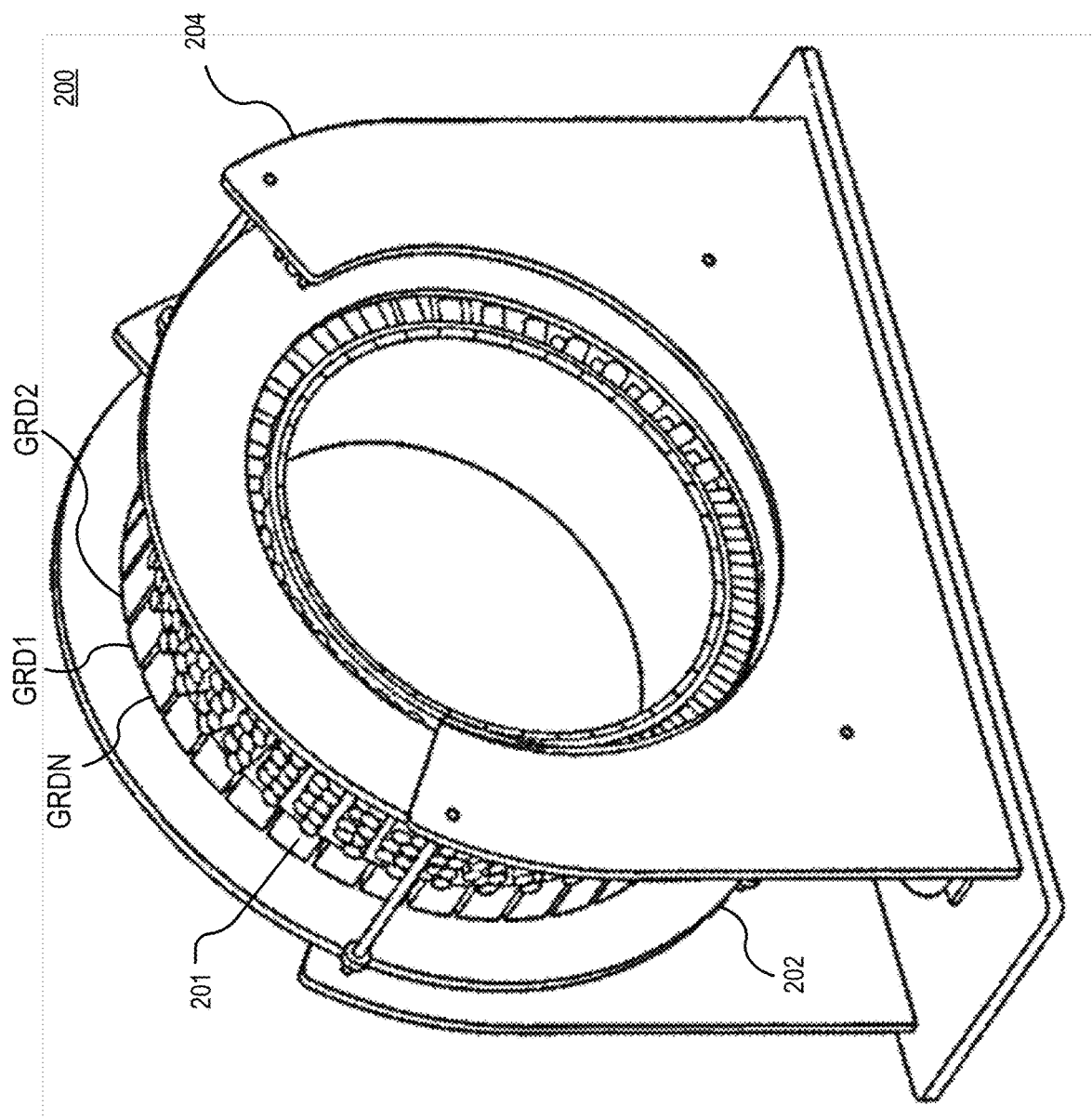

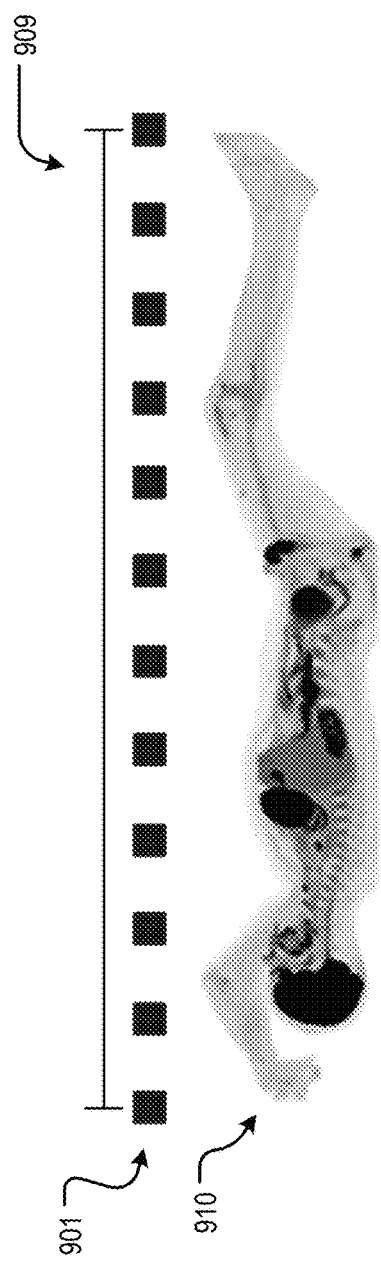
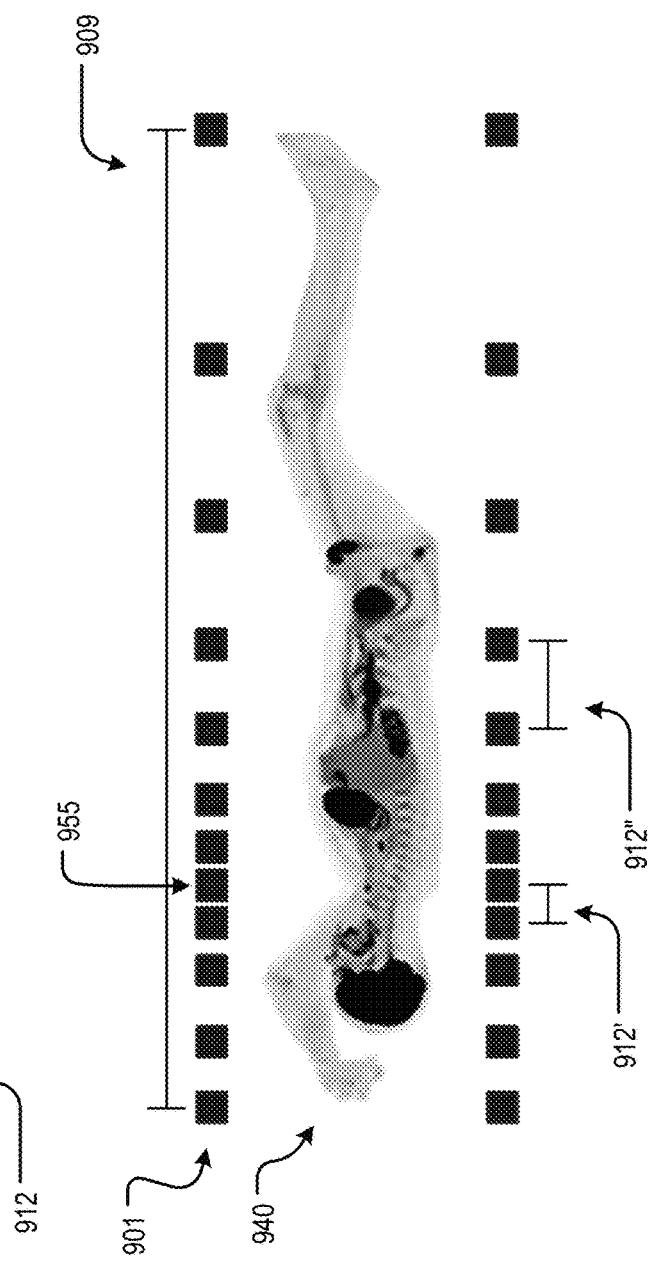
FIG. 9A
FIG. 9B

PET RECONSTRUCTION FOR ADJUSTABLE PET SYSTEM

BACKGROUND

Field of the Disclosure

The present disclosure relates to diagnostic imaging systems and methods. In particular, the present disclosure relates to positron emission tomography.

Description of the Related Art

Positron emission tomography (PET) imaging begins with the administration (e.g., through ingestion or inhalation) of a radiopharmaceutical agent to a patient. In time, the radiopharmaceutical agent concentrates at specific locations in the human body, thereby exploiting physical and biomolecular properties of the radiopharmaceutical agent to accumulate at regions of interest. The actual spatial distribution, intensity of the point or region of accumulation, and kinetics of the PET imaging process, from administration to capture to elimination, are all elements that may have clinical significance.

During the PET imaging process, the positron emitter attached to the pharmaceutical agent will emit positrons according to the physical properties of the isotope. Emitted positrons collide with an electron of the imaging object, or patient, resulting in an annihilation of the positron and electron and generation of two gamma rays at 511 keV in opposite directions. PET scanners, which include several PET detector rings for detecting the generated gamma rays, typically include a cylindrical bore-type housing supporting the several PET detector rings. These PET scanners typically have a field of view with fixed axial dimensions and radial dimensions. In order to allow for increasing size of patients and increasing clinical demands, commercial PET scanners have been developed with increasingly large bore diameters and axial lengths. However, such designs increase PET scanner cost as the number of detectors and detector rings, which drive system costs, increases with bore diameter and axial length.

Appreciating that the axial dimension of a field of view of a PET scanner is typically fixed, increasing the axial field of view (aFOV) without, concomitantly, increasing the number of PET detector modules and rings (and hence increased cost), requires the introduction of larger gaps between adjacent PET detector rings. The aFOV of the system is, therefore, the sum of the axial dimension of the rings and the gaps between the rings. Though providing adequate sensitivity in certain applications, such an aFOV system suffers from a decreased signal-to-noise ratio and loss of incident events that may occur within the gaps between adjacent PET detector rings. In addition, an increased aFOV may not be appropriate for all applications. For instance, an increased aFOV may be appropriate for imaging a whole torso but may be unable to capture information specifically-relevant to a lung cancer.

Accordingly, an adaptive approach to PET detector ring positioning is required, as will be described in the present disclosure.

The foregoing "Background" description is for the purpose of generally presenting the context of the disclosure. Work of the inventors, to the extent it is described in this background section, as well as aspects of the description which may not otherwise qualify as prior art at the time of filing, are neither expressly or impliedly admitted as prior art against the present invention.

SUMMARY

The present disclosure relates to a positron emission tomography scanner and methods for axially-adjustable detector module rings.

According to an embodiment, the present disclosure further relates to a positron emission tomography scanner, comprising a plurality of gamma-ray detector rings that form a bore through which an imaging subject is translated, a length of the bore defining an axial length of the PET scanner, the plurality of gamma-ray detector rings being movable along the axial length, the plurality of gamma-ray detector rings each including gamma-ray detector modules therein, and processing circuitry configured to receive PET data associated with a plurality of transaxial slices of the imaging subject, the PET data including a first set of spatial information and timing information corresponding to a first data acquisition period for the gamma-ray detector modules in a first axial position along the axial length and a second set of spatial information and timing information corresponding to a second data acquisition period for the gamma-ray detector modules in a second axial position along the axial length, and reconstruct a PET image based on the received PET data, including the first set of spatial information and timing information and the second set of spatial information and timing information.

According to an embodiment, the present disclosure further relates to a method of a positron emission tomography scanner, comprising receiving, by processing circuitry, PET data associated with a plurality of transaxial slices of an imaging subject, the imaging subject being translated through a bore defined by a plurality of gamma-ray detector rings positioned along a length of the bore defining an axial length of the PET scanner, the plurality of gamma-ray detector rings each including gamma-ray detector modules therein, the PET data including a first set of spatial information and timing information corresponding to a first data acquisition period for the gamma-ray detector modules in a first axial position along the axial length and a second set of spatial information and timing information corresponding to a second data acquisition period for the gamma-ray detector modules in a second axial position along the axial length; and reconstructing, by the processing circuitry, a PET image based on the first set of spatial information and timing information and the second set of spatial information and timing information.

According to an embodiment, the present disclosure further relates to a non-transitory computer-readable storage medium storing computer-readable instructions that, when executed by a computer, cause the computer to perform a method of a positron emission tomography scanner, comprising receiving, by processing circuitry, PET data associated with a plurality of transaxial slices of an imaging subject, the imaging subject being translated through a bore defined by a plurality of gamma-ray detector rings positioned along a length of the bore defining an axial length of the PET scanner, the plurality of gamma-ray detector rings each including gamma-ray detector modules therein, the PET data including a first set of spatial information and timing information corresponding to a first data acquisition period for the gamma-ray detector modules in a first axial position along the axial length and a second set of spatial information and timing information corresponding to a second data acquisition period for the gamma-ray detector modules in a second axial position along the axial length; and reconstructing, by the processing circuitry, a PET image based on the first set of spatial information and timing information and the second set of spatial information and timing information.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 1A is an illustration of detector module rings within a short axial field of view of a PET scanner;

FIG. 1B is an illustration of detector module rings within a long axial field of view of a PET scanner;

FIG. 2 is an illustration of a perspective view of a positron emission tomography (PET) scanner;

FIG. 9A is an illustration of an axial field of view PET scanner;

FIG. 9B is an illustration of a method of an adaptive axial field of view PET scanner, according to an exemplary embodiment of the present disclosure;

DETAILED DESCRIPTION

Figure 1C:
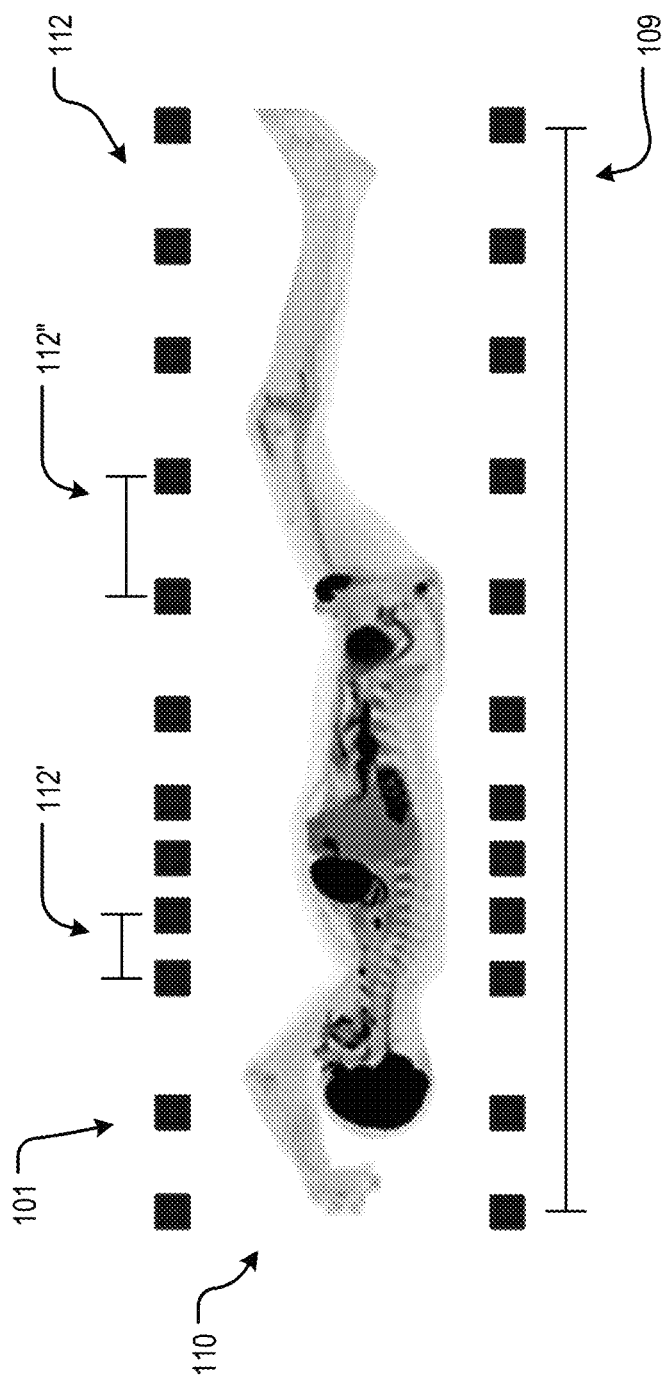
FIG. 1C is an illustration of detector module rings within an adaptive axial field of view, according to an exemplary embodiment of the present disclosure.

The terms "a" or "an", as used herein, are defined as one or more than one. The term "plurality", as used herein, is defined as two or more than two. The term "another", as used herein, is defined as at least a second or more. The terms "including" and/or "having", as used herein, are defined as comprising (i.e., open language). Reference throughout this document to "one embodiment", "certain embodiments", "an embodiment", "an implementation", "an example" or similar terms means that a particular feature, structure, or characteristic described in connection with the embodiment is included in at least one embodiment of the present disclosure. Thus, the appearances of such phrases or in various places throughout this specification are not necessarily all referring to the same embodiment. Furthermore, the particular features, structures, or characteristics may be combined in any suitable manner in one or more embodiments without limitation.

All nuclear medicine studies in humans are limited by the trade-offs between the number of detected decay events, imaging time, and absorbed dose. The number of detected events determines the signal-to-noise ratio (SNR) in the final image, but constraints on administered activity, as well as high random event rates and dead time that occur at high activities, currently prevent acquisition of high-SNR images in short times. This in turn limits the ability to perform high-resolution, dynamic imaging studies with tracer kinetic modeling, because short—time-frame datasets are always noisy. A further limitation is that although the tracer injection is systemic and radiotracer is present in the entire body of a patient, current imaging systems contain only a small portion of the body of the patient within a field of view (FOV) thereof. For applications in which the distribution of radiotracer in the entire body or multiple organ systems of the patient is of interest, this limitation leads to further inefficiencies and makes it difficult to acquire dynamic data from all the tissues of interest.

Understanding the FOV is generally fixed, acquiring dynamic data from all the tissues of interest may require translation of a table of a positron emission tomography (PET) scanner relative to PET detector rings thereof and, via post-processing, stitching time mismatched images in order to approximate real-time tracer data. Further, if one considers whole-body PET scanning with fluorodeoxyglucose F 18 (18F-FDG), as an example, wherein the table of the PET scanner is translated relative to the PET detector rings and successive images are acquired, the total efficiency with which pairs of coincidence photons that escape the body are detected is under 1%. Simplistically, this number can be derived by considering that the average geometric sensitivity within the FOV of a typical clinical PET scanner is under 5% and that with an axial coverage of 20 cm, less than an eighth of the body is in the FOV at any one time.

Therefore, it can be appreciated that improving geometric coverage of a PET scan by, for instance, using a total-body PET scanner that provides a field of view matching a size and a length of a patient, may directly increase sensitivity by over an order of magnitude. Such a large improvement in effective sensitivity has the potential to dramatically broaden the utility of PET in human medical research, potentially leading to new clinical applications and improve its utility in existing clinical applications.

In order to achieve a total-body PET scanner with meaningful diagnostic value for all patients and disease conditions, however, a cost-prohibitive number of PET detector rings, and detector elements thereof, is required. As a result, investigations have focused on cost-effective methods for providing a long FOV, also referred to as a long axial FOV or long aFOV, which approximates the advantages of total-body PET scanning. In order to reduce costs, such investigations have minimized the number of detector elements required by introducing gaps between adjacent PET detector rings. While providing similar sensitivity, spatial resolution, and contrast recovery to short aFOV approaches, in addition to providing fixed PET detector ring positions, long aFOV approaches increase image noise while failing to capture information present within the gaps between adjacent PET detector rings.

Moreover, a long aFOV may not be necessary for all clinical applications. For example, and as has similarly plagued use of total-body PET scanners, pediatrics or organ-specific protocols, such as brain imaging or cardiac imaging, may not require use of a long axial FOV. Even in instances where a long aFOV PET scanner is theoretically useful, the sensitivity thereof is not always needed to provide useful diagnostic data, as in the case of whole-torso imaging for lung cancer or whole-body measurement of FDG-standardized uptake values (SUV).

As a result, and with reference now to FIG. 1A and FIG. 1B, clinicians, radiologists, and hospitals are faced with the decision of either utilizing a fixed, short aFOV PET scanner, as in FIG. 1A, that can acquire high SNR data within a small region of interest of a patient 110, or a long aFOV PET scanner, as in FIG. 1B, that can acquire, within a large aFOV 109, a large region of interest of a patient 110 but with data voids in the gaps formed between adjacent PET detector rings 101. This is shown in FIG. 1A, where the short aFOV PET scanner may employ PET detector rings 101, configured to detect gamma-rays, at minimal PET detector ring spacing 112, and in FIG. 1B, where the long axial FOV PET scanner may employ PET detector rings 101 at larger PET detector ring spacing 112.

When an emitted positron from a phantom or human collides with an electron, an annihilation event occurs, wherein the positron and electron are combined. Most of the time, the annihilation event produces two gamma rays (at 511 keV) traveling at substantially 180 degrees apart. One of these gamma rays can be referred to as a single. To reconstruct the spatio-temporal distribution of the tracer via tomographic reconstruction principles, each detected event is characterized for its energy (i.e., amount of light generated), its location, and its timing. By detecting the two gamma rays (i.e., two of the singles, or a pair), and drawing a line between their locations, i.e., a line-of-response (LOR), one can determine the likely location of the original disintegration.

In addressing the above-described issues faced with rigid, fixed, aFOV PET scanners, the present disclosure describes a 'flexible', axially-adaptive FOV PET scanner. Introduced now with reference to FIG. 1C, an adaptive aFOV (aaFOV) PET scanner system, according to an exemplary embodiment of the present disclosure, provides adjustable PET detector rings that may be positioned in areas of diagnostic relevance according to patient size, shape, and medical imaging. As in FIG. 1C, PET detector rings 101 may be arranged along an aFOV 109 corresponding to an axial length of a patient 110 in order to provide total-body imaging. According to methods of the aaFOV PET scanner, the PET detector rings 101 may be positioned according to certain features of the patient including patient age, patient gender, and patient height, or according to radiation attenuation within the patient based on medical imaging. In this way, certain regions of the patient 110 may have PET detector ring spacing 112' of a first distance and certain other regions of the patient 110 may have PET detector ring spacing 112" of a second distance, as dictated by relevant patient factors. For instance, and as in FIG. 1C, a region of interest may include the upper respiratory tract of the patient 110 and, accordingly, the PET detector ring spacing 112' of the upper torso may be shorter than the PET detector ring spacing 112" of the lower extremities. Of course, it may also be the case that an axial length of the patient, or patient height, is longer than the aFOV of the aaFOV PET scanner during imaging, as the aFOV may be adjusted to be the length of the patient or to be a subset, thereof, in order to provide appropriate imaging conditions.

The methods of the present disclosure, introduced above with reference to FIG. 1C, will be described in detail with reference to the remaining Figures.

According to an embodiment, the present disclosure describes a PET scanner having axially-adjustable detector ring positions and methods by which the axially-adjustable detector rings are adjusted. In an embodiment, the PET detector ring positions, which may be interchangeably referred to herein as detector ring positions, may be adjusted according to specified constraints. For instance, a user may specify an axial position which is intended to have a focal point with high sensitivity, and detector ring positions may be determined and adjusted according thereto. The PET scanner allows, in an embodiment, manual adjustment of detector ring axial positions.

In an embodiment, PET detector ring positions may be adjusted automatically, based upon patient features and/or prior medical imaging. For instance, the detector ring positions may be adjusted according to physical parameters, or biometrics, of a patient. Detector ring positions may be determined according to table-mounted weight sensors, external optical sensors, gantry-mounted distance sensors, and the like. Such determinations may be made automatically according to methods described herein.

In an embodiment, the detector ring positions may be automatically adjusted according to patient-derived image profiles. For instance, detector ring positions may be determined according to transaxial slices of a computed tomography (CT) scan of the patient. In particular, the detector ring positions may be based on a CT mask size or CT intensity metrics such as a sum, a median, a maximum, and a power of sum, among other statistical metrics. In another instance, detector ring positions may be determined according to a PET scan of a patient or a region of interest of a patient. In particular, the detector ring positions may be determined according to a PET scan of a skull of a patient and may be based on a PET mask size of the skull of the patient or PET intensity metrics of the skull of the patient, such as a sum, a median, a maximum, and a power of sum, among other statistical metrics. In an embodiment, the detector ring positions may be adjusted according to a predefined model. For instance, a predefined model for the detector ring positions may be selected based on patient biometric information such as height, weight, and gender, among others, and/or patient diagnostic information. The above-introduced methods will be described in further detail below.

According to an embodiment, the detector ring positions may be determined according to a central region of interest of a patient and a peripheral region of interest of the patient. For instance, one or more detector rings may be positioned within the peripheral region of interest in order to enable improved scatter estimation therein during reconstruction of an image based on data acquired from the central region of interest.

Figure 3:
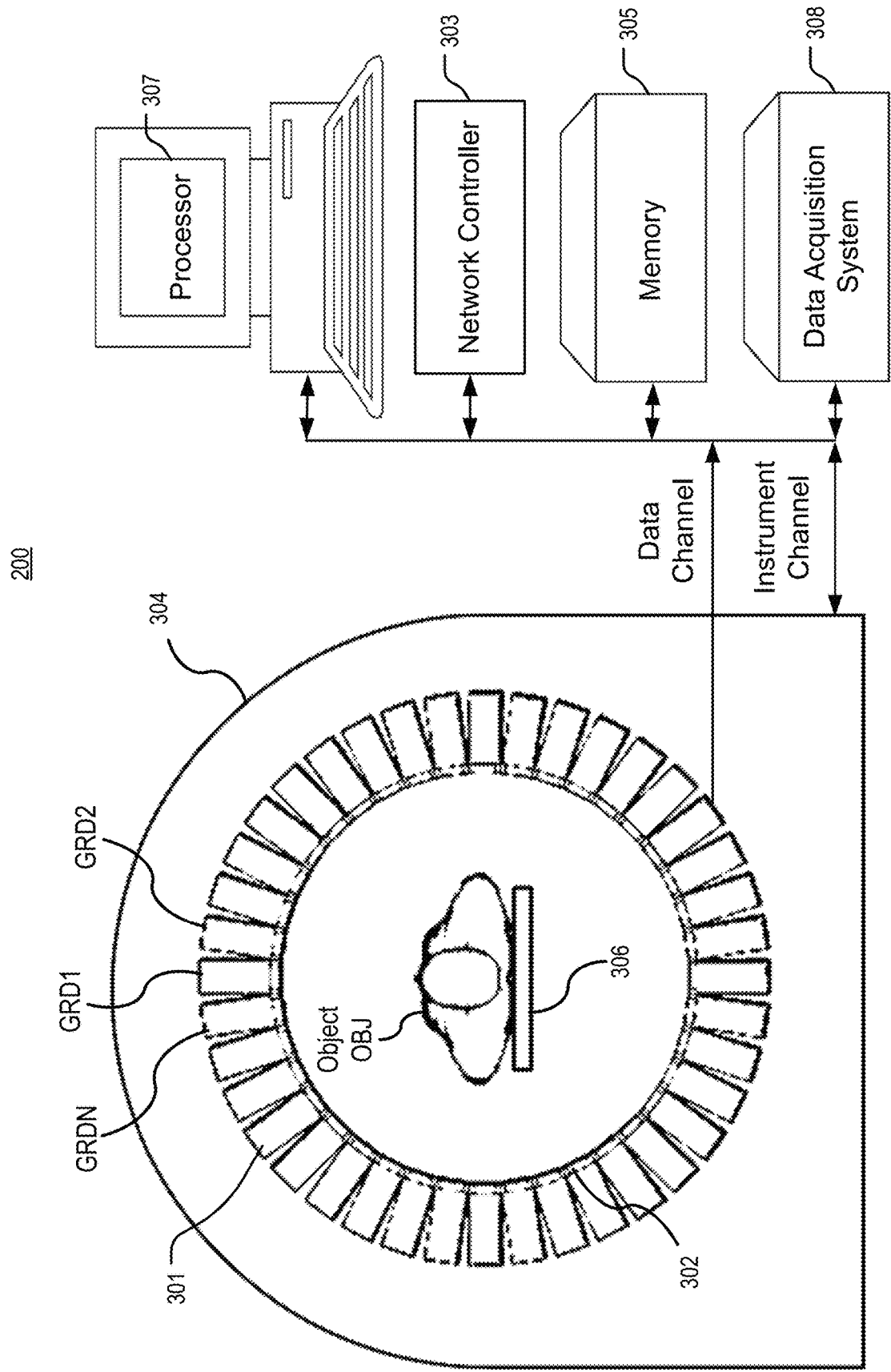
FIG. 3 is a schematic of a PET scanner and associated hardware, according to an exemplary embodiment of the present disclosure.

The above introduction will now be further described with reference to the Figures, wherein like reference numerals designate identical or corresponding parts throughout the several views. It can be appreciated that the methods of the present disclosure may be implemented within a PET scanner, as shown in FIG. 2 and FIG. 3. Therefore, FIG. 2 and FIG. 3 show a PET scanner 200 including a number of gamma-ray detectors (GRDs) 201 (e.g., GRD1, GRD2, through GRDN) that are each configured as rectangular detector modules. The PET scanner 200 may be an aaFOV PET scanner, as introduced above. According to one implementation, each PET detector ring, which forms a circular bore 202 about a gantry 204, includes 40 GRDs. In another implementation, there are 48 GRDs, the higher number of GRDs being used to create a larger bore size for the PET scanner 200. As in the present disclosure, each PET detector ring may be independently translatable about an axial length of the aaFOV PET scanner. The translation of each PET detector ring may be accomplished by manual manipulation and/or motorized manipulation. The GRDs include scintillator crystal arrays for converting the gamma rays into scintillation photons (e.g., at optical, infrared, and ultraviolet wavelengths), which are detected by photodetectors. Each GRD can include a two-dimensional array of individual detector crystals, which absorb gamma radiation and emit scintillation photons. The scintillation photons can be detected by a two—dimensional array of photomultiplier tubes (PMTs) that are also arranged in the GRD. A light guide can be disposed between the array of detector crystals and the PMTs. Further, each GRD can include a number of PMTs of various sizes, each of which is arranged to receive scintillation photons from a plurality of detector crystals. Each PMT can produce an analog signal that indicates when scintillation events occur, and an energy of the gamma ray producing the detection event. Moreover, the photons emitted from one detector crystal can be detected by more than one PMT, and, based on the analog signal produced at each PMT, the detector crystal corresponding to the detection event can be determined using Anger logic and crystal decoding, for example. However, Anger arithmetic is not necessarily required when there is a one-to-one correspondence between the crystals and the photodetectors.

FIG. 3 shows a schematic view of a PET scanner system having GRDs arranged to detect gamma-rays emitted from an object OBJ. The GRDs can measure the timing, position, and energy corresponding to each gamma-ray detection. In one implementation, the gamma-ray detectors are arranged in a PET detector ring, as shown in FIG. 2 and FIG. 3, and as described herein. It can be appreciated that the single PET detector ring of FIG. 3 can be extrapolated to include any number of PET detector rings along an axial length of the PET scanner. The detector crystals can be scintillator crystals, which have individual scintillator elements arranged in a two-dimensional array and the scintillator elements can be any known scintillating material. The PMTs can be arranged such that light from each scintillator element is detected by multiple PMTs to enable Anger arithmetic and crystal decoding of scintillation event.

FIG. 3 shows an example of the arrangement of the PET scanner 200, in which the object OBJ to be imaged rests on a table 306 and the GRD modules GRD1 through GRDN are arranged circumferentially around the object OBJ and the table 306. The GRDs may comprise a PET detector ring and may fixedly-connected to a circular bore 302 that is fixedly-connected to a gantry 304. The gantry 304 houses many parts of the PET scanner. The gantry 304 of the PET scanner also includes an open aperture, defined by the cylindrical bore 302, through which the object OBJ and the table 306 can pass, and gamma-rays emitted in opposite directions from the object OBJ due to an annihilation event can be detected by the GRDs and timing and energy information can be used to determine coincidences for gamma-ray pairs.

Figure 4:
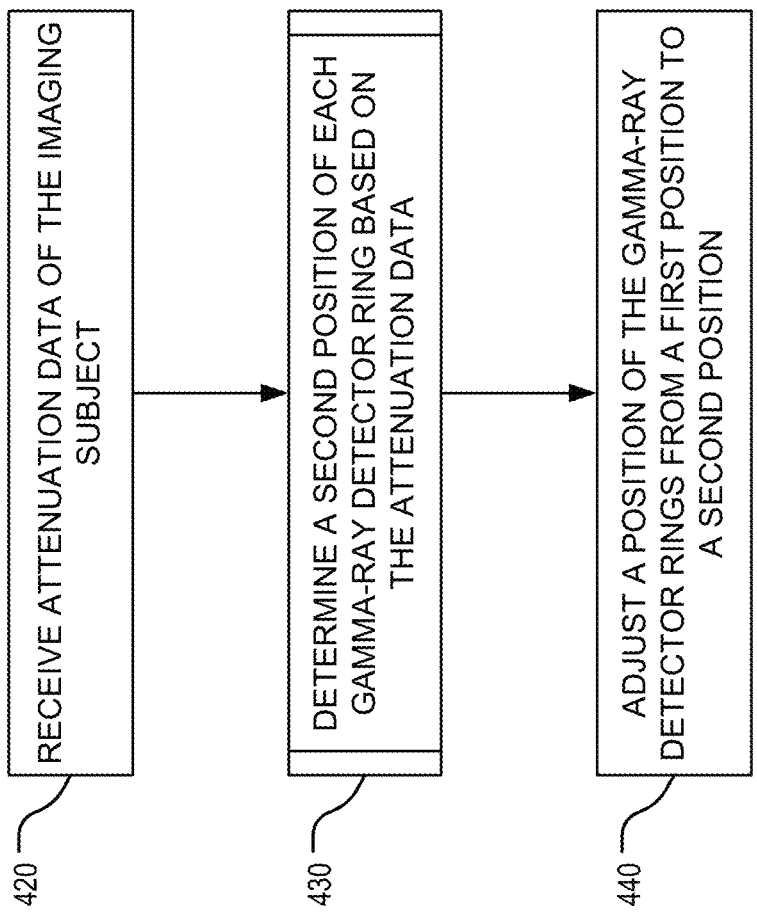
FIG. 4 is a flow diagram of a method of an adaptive axial field of view PET scanner, according to an exemplary embodiment of the present disclosure.

In FIG. 3, circuitry and hardware is also shown for acquiring, storing, processing, and distributing gamma-ray detection data. The circuitry and hardware include a processor 307, a network controller 303, a memory 305, and a data acquisition system (DAS) 308. The PET imager also includes a data channel that routes detection measurement results from the GRDs to the DAS 308, the processor 307, the memory 305, and the network controller 303. The data acquisition system 308 can control the acquisition, digitization, and routing of the detection data from the detectors. In one implementation, the DAS 308 controls the movement of the table 306. The processor 307 performs functions including adjusting PET detector rings in accordance with method 415 (which is illustrated in FIG. 4 and described below), pre-reconstruction processing of the detection data, image reconstruction, and post-reconstruction processing of the image data.

According to an embodiment, the processor 307 of the PET scanner 200 of FIG. 2 and FIG. 3 can be configured to perform method 415, as described herein. The processor 307 can include a CPU that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the memory 305 can be a hard disk drive, CD-ROM drive, DVD drive, FLASH drive, RAM, ROM or any other electronic storage known in the art. The memory 305 may be non-volatile, such as ROM, EPROM, EEPROM or FLASH memory. The memory 305 can also be volatile, such as static or dynamic RAM, and a processor, such as a microcontroller or microprocessor, may be provided to manage the electronic memory as well as the interaction between the FPGA or CPLD and the memory.

Alternatively, the CPU in the processor 307 can execute a computer program including a set of computer-readable instructions that perform method 415 described herein, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a Xenon processor from Intel of America or an Opteron processor from AMD of America and an operating system, such as Microsoft VISTA, UNIX, Solaris, LINUX, Apple, MAC-OS and other operating systems known to those skilled in the art. Further, CPU can be implemented as multiple processors cooperatively working in parallel to perform the instructions.

In one implementation, the PET scanner may include a display for displaying a reconstructed image and the like. The display can be an LCD display, CRT display, plasma display, OLED, LED or any other display known in the art.

The network controller 303, such as an Intel Ethernet PRO network interface card from Intel Corporation of America, can interface between the various parts of the PET imager. Additionally, the network controller 303 can also interface with an external network. As can be appreciated, the external network can be a public network, such as the Internet, or a private network such as an LAN or WAN network, or any combination thereof and can also include PSTN or ISDN sub-networks. The external network can also be wired, such as an Ethernet network, or can be wireless such as a cellular network including EDGE, 3G and 4G wireless cellular systems. The wireless network can also be WiFi, Bluetooth, or any other wireless form of communication that is known.

The methods of an aaFOV PET scanner system, as introduced above, will now be described with reference to the remaining Figures.

With reference to FIG. 4, method 415 describes an exemplary embodiment of the present disclosure. Generally, the method 415 may be implemented within an aaFOV PET scanner and relies on data from a CT scan of a patient to be imaged in order to define PET detector ring positions relative to the patient and an axial length of the CT scanner. The CT scanner and the aaFOV PET scanner may be the same machine. In this way, based on the CT scan of the patient, the PET detector rings may be moved from a first position to a second position in order to provide improved imaging capabilities in a specific region of interest.

In particular, beginning at step 420 of method 415, attenuation data of a patient may be received. The attenuation data may be attenuation count data from each transaxial slice of a CT scan of the patient. The attenuation count data may define, for each transaxial slice of the CT scan of the patient, an amount of energy that is absorbed by a specific region of a patient along an axial length of the patient. The CT scan may be, necessarily, a full-body CT scan.

At sub process 430 of method 415, the attenuation data received at step 420 of method 415 may be used to determine a second position of each PET detector ring, or gamma-ray detector ring. The second positions may be determined according to a count number and a mask size, among other factors appropriate for a specific imaging condition.

At step 440 of method 415, the second positions determined at sub process 430 of method 415 can be used to adjust the PET detector rings from their first positions.

Of course, in an embodiment, the above describe method 415 may be implemented on the basis of a PET scan of a region of interest of the patient. The region of interest may be a skull, in an example, but resulting data may be treated by method 415, described above and below, similarly to the attenuation data acquired from the CT scan. In this instance, implementation on a skull of a patient may reduce radiation exposure while attaining useful information.

Figure 5:
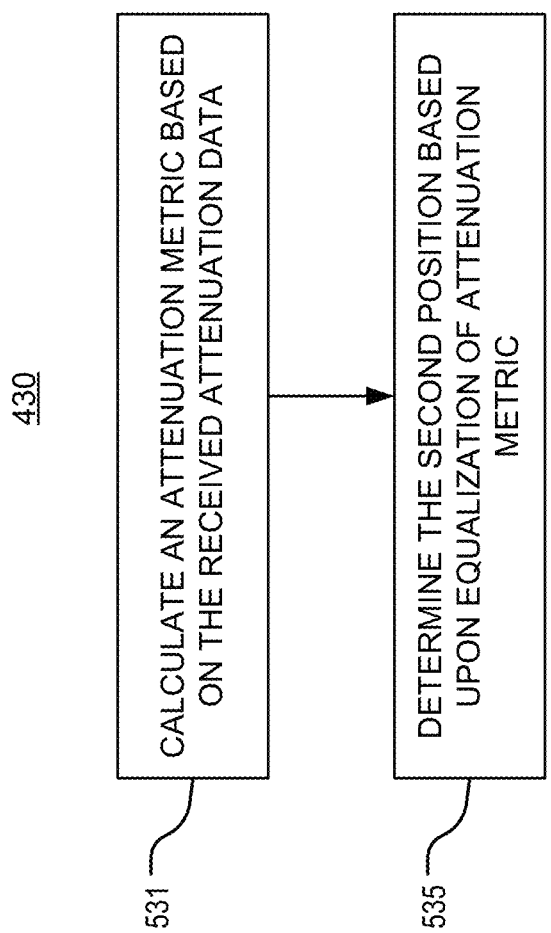
FIG. 5 is a flow diagram of a sub process of a method of an adaptive axial field of view PET scanner, according to an exemplary embodiment of the present disclosure.

Sub process 430 of method 415 will now be described with reference to FIG. 5. At step 531 of sub process 430, an attenuation metric may be calculated based on the received attenuation data. The attenuation metric may be determined in view of the first positions of each of the PET detector rings. The attenuation metric may be, in an example, an area under a curve between adjacent PET detector rings, the curve describing attenuation counts relative to transaxial slice number of a CT scan. The attenuation metric may be, in another example, an area of an attenuation mask between adjacent PET detector rings, the attenuation mask reflecting a shape of the patient, or attenuating body, as determined from attenuation count data. In this way, it can be appreciated that, pursuant to the first positions of the PET detector rings, a comparison of the attenuation metrics between adjacent PET detector rings would reveal varying attenuation metric values. Accordingly, at step 535 of sub process 430, and in order to determine the second position of each PET detector ring, the attenuation metric calculated between each adjacent PET detector ring may be equalized by adjusting a position of each PET detector ring to a second position. The second position, therefore, may result in the attenuation metric between adjacent PET detector rings being equal along the axial length of the PET scanner.

Figure 6A:
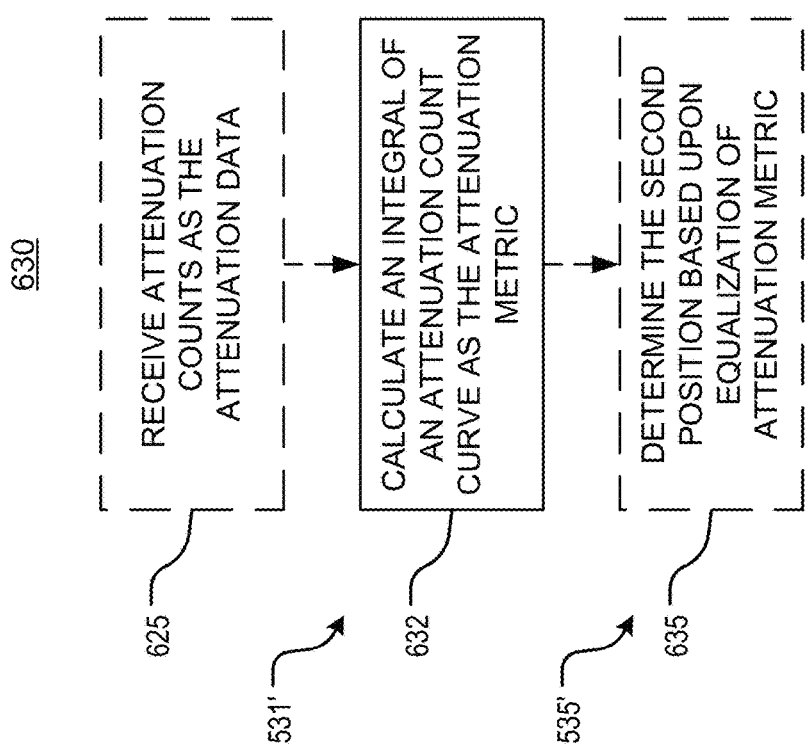
FIG. 6A is a flow diagram of a sub process of a method of an adaptive axial field of view PET scanner, according to an exemplary embodiment of the present disclosure.
Figure 6B:
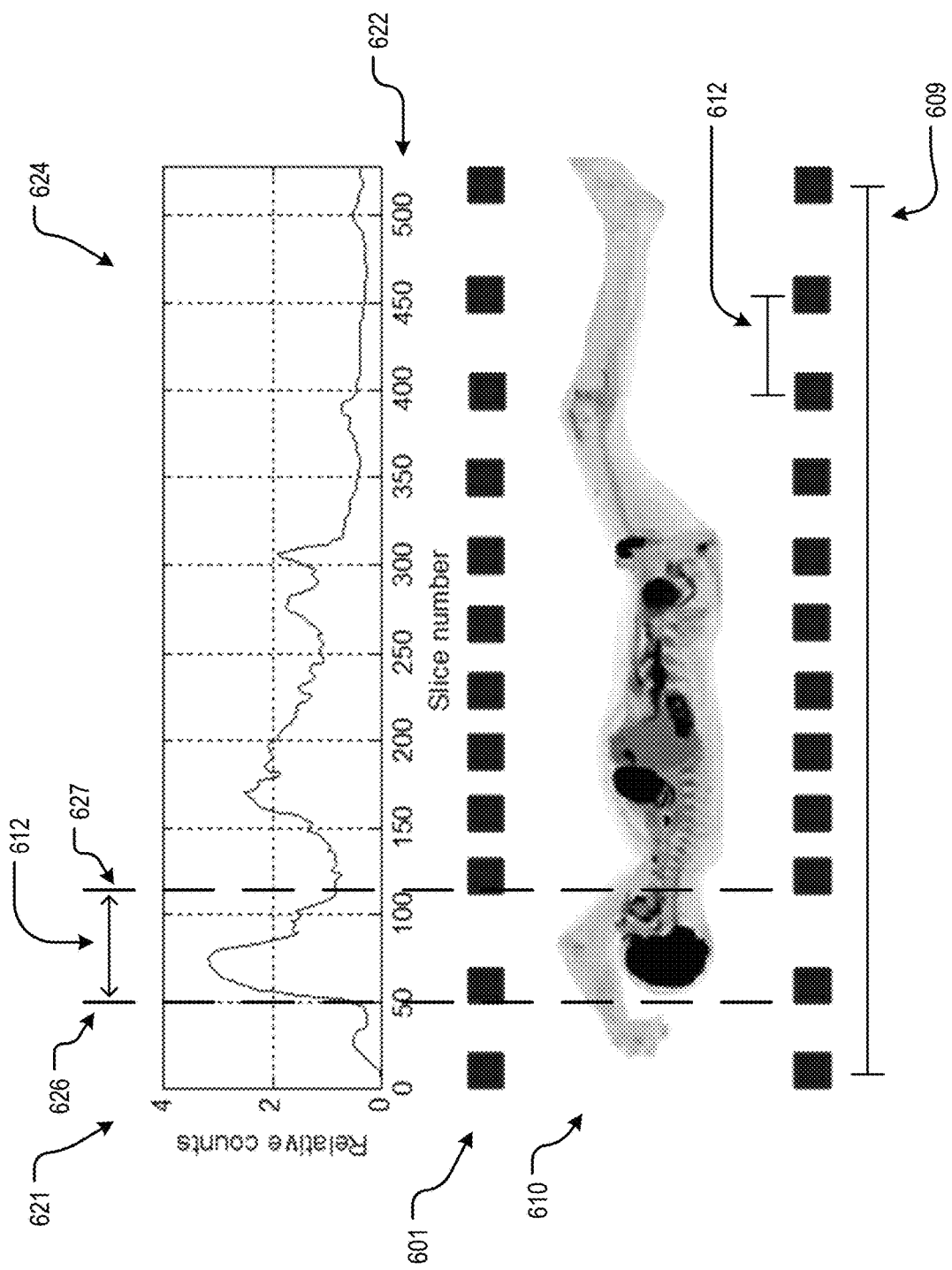
FIG. 6B is an illustration of a sub process of a method of an adaptive axial field of view PET scanner, according to an exemplary embodiment of the present disclosure.

According to an embodiment, and as will be described with reference to the flow diagram of FIG. 6A and the illustration of FIG. 6B, the attenuation metric may be an area under the curve (AUC) of an attenuation count curve 624, the AUC of the attenuation count curve 624 describing an accumulation of radiation within a given physical area of the patient.

At step 625, attenuation count data may be received as the attenuation data. The attenuation count data may be determined from a CT scan performed on a patient prior to PET imaging. The attenuation count data may include, as in FIG. 6B, attenuation counts 621 relative to transaxial slice number 622 of the CT scan.

At step 632 of sub process 630, which is an example (531') of step 531 of sub process 430, the attenuation counts of the attenuation data received at step 625 may be processed to calculate, as the attenuation metric, an integral between adjacent PET detector rings 601 in first positions, relative to the attenuation count curve 624. In this way, a comparison between AUCs of each set of adjacent PET detector rings 601, in first positions, may determine a lack of parity in the system.

Accordingly, assuming the attenuation metric is not equalized in the PET detector ring first positions, second positions of each of the PET detector rings 601 may be determined at step 635 of sub process 630 such that AUCs of each set of adjacent PET detector rings 601 is equal. Step 635 is an example (535') of step 535 of sub process 430. In view of FIG. 6B, this may mean that PET detector rings 601 near a torso of a patient 610 are closer together than PET detector rings 601 near feet of the patient 610 in order to normalize the attenuation counts 621 across an aFOV 609 of the patient 610. As can be seen in view of the aFOV 609 which includes the upper extreme positions and lower extreme positions of the patient 610 (i.e., a length of the patient 610, in part, dictates the aFOV 609), the aaFOV PET scanner described herein provides diagnostically useful total-body imaging by varying PET detector ring spacing 612 in accordance with the AUCs of the attenuation count curve 624.

Step 635 of sub process 630 may be determined mathematically. In view of dashed lines 626, 627 of FIG. 6B, which indicate second positions of PET detector rings 601, it can be appreciated that an AUC between the dashed lines 626, 627 reflects the attenuation counts 621 relative to transaxial slices 622 of a CT scan. In order to normalize the AUC of the attenuation count curve 624 between adjacent PET detector rings 601, the following algorithm may be implemented.

In an embodiment, the attenuation count curve 624 may be described as a $$y=f(n), n=0,\ldots,N$$

where f (n) is a curve defined by attenuation counts 621 relative to transaxial slice number 622, and N is the total number of transaxial slices. In order to determine PET detector ring spacing 612, the following formula can be satisfied:

$$\int_{x_i}^{x_{i+1}} f(n) = \frac{\int_0^N f(n)}{M}$$

where M is a number of PET detector rings and $x_i$ and $x_{i+1}$ correspond to positions of a PET detector ring positioned at a first dashed line 626 and to a PET detector ring positioned at a second dashed line 627, respectively, but may correspond to any adjacent PET detector rings arranged along the aFOV 609 of the patient 610. In satisfying the above-described equation, a distance 612 between PET detector rings 601 may be determined such that, when the PET detector rings 601 are in the second position, an AUC is equal between each "gap" between the PET detector rings 601.

Figure 7A:
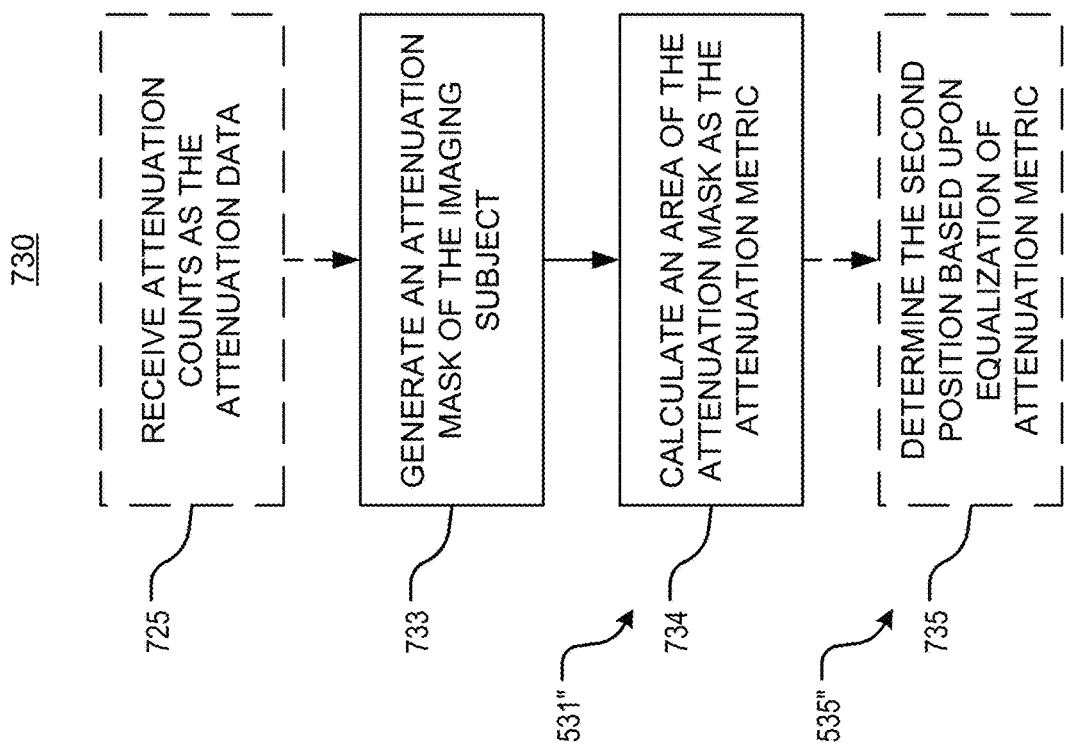
FIG. 7A is a flow diagram of a sub process of a method of an adaptive axial field of view PET scanner, according to an exemplary embodiment of the present disclosure.

According to an embodiment, and as will be described with reference to the flow diagram of FIG. 7A and the illustration of FIG. 7B, the attenuation metric may be an area of an attenuation mask 728 of a patient 710 between adjacent PET detector rings 701 along an aFOV 709 of the patient 710.

At step 725, attenuation count data may be received as the attenuation data. The attenuation count data may be determined from a CT scan performed on a patient prior to PET imaging. The attenuation count data may include attenuation counts relative to transaxial slice number 722 of the CT scan.

Figure 7B:
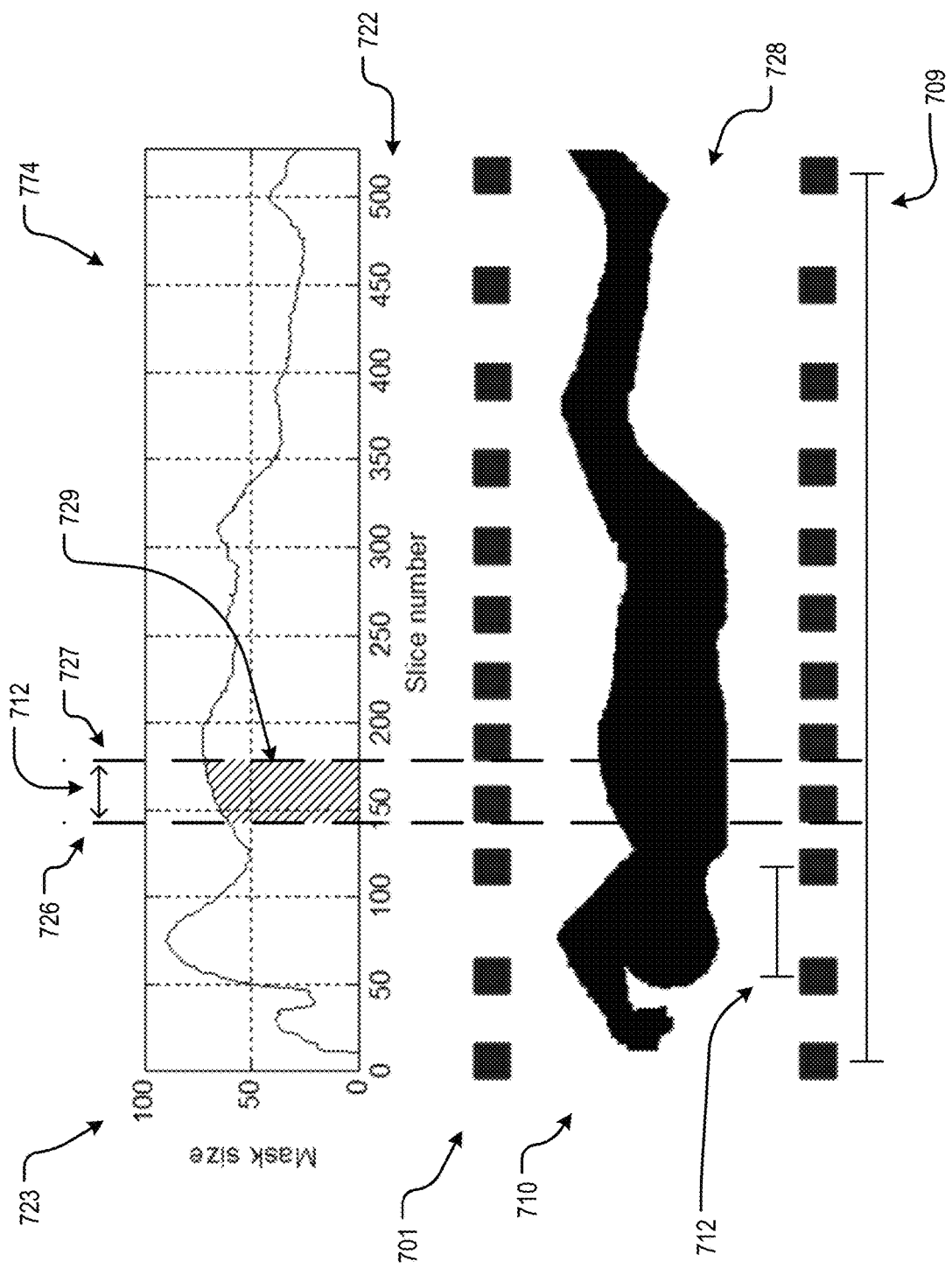
FIG. 7B is an illustration of a sub process of a method of an adaptive axial field of view PET scanner, according to an exemplary embodiment of the present disclosure.

At step 733 of sub process 730, the attenuation counts of the attenuation data received at step 725 may be processed to generate an attenuation mask 728 of the patient 710, as shown in FIG. 7B. The attenuation mask 728 may be based on attenuation counts from the attenuation data to determine a cross-sectional geometry, or mask size 723, of the patient 710 at each transaxial slice number 722, appreciating that attenuation effectively identifies positions within the PET scanner where the patient is located. In this way, the attenuation data may be used to determine physical size features of the patient 710 instead of attenuating characteristics, thereof. The mask size 723 of the patient 710 at each transaxial slice number 722 defines an attenuation mask size curve 774.

The attenuation mask 728 generated at step 733 of sub process 730 may be used to calculate the AUC, as the attenuation metric, at step 734 of sub process 730. Step 734 of sub process 730 is an example (531") of step 531 of sub process 430. An AUC 729 of the attenuation mask size curve 774 is an exemplary AUC, as described herein. The AUC may be calculated by integrating the attenuation mask size curve 774 between adjacent PET detector rings 701 in first positions. In this way, a comparison between AUCs of each set of adjacent PET detector rings 701, in first positions, may determine a lack of parity in the system. As described with respect to FIG. 7A, the AUC may describe a cross-sectional geometry of the patient 710, based on the attenuation mask 728.

Accordingly, and assuming the first positions of the PET detector rings of the aaFOV PET scanner do not equalize the attenuation metric, second positions of each of the PET detector rings 701 may be determined at step 735 of sub process 730 such that AUCs of each set of adjacent PET detector rings 701 is equal. Step 735 is an example (535") of step 535 of sub process 430. In view of FIG. 7B, this may mean that PET detector rings 701 near an abdomen of a patient 710, where the patient 710 may be larger, are closer together than PET detector rings 701 near feet of the patient 710 in order to normalize the mask size 723 across an aFOV 709 of the patient 710. As can be seen in view of the aFOV 709 which includes the upper and lower extreme positions of the patient 710 (i.e., a length of the patient 710, in part, dictates the aFOV 709), the aaFOV PET scanner described herein provides diagnostically useful total-body imaging by varying PET detector ring spacing 712 in accordance with the AUCs of the attenuation mask size curve 774.

Step 735 of sub process 730 may be determined mathematically. In view of dashed lines 726, 727 of FIG. 7B, which indicate second positions of PET detector rings 701, it can be appreciated that an AUC between the dashed lines 726, 727 reflects the attenuation mask size 723 relative to transaxial slices 722 of a CT scan. In order to normalize the AUC of the attenuation mask size curve 774 between adjacent PET detector rings 701, the following algorithm may be implemented.

In an embodiment, the attenuation mask size curve 774 may be described as a $$y=f(n), n=0,\ldots,N$$

where f(n) is a curve defined by attenuation mask size 623 relative to transaxial slice number 622 and N is the total number transaxial slices 722. In order to determine PET detector ring spacing 712, the following formula need be satisfied $$\int_{x_i}^{x_{i+1}} f(n) = \frac{\int_0^N f(n)}{M}$$

where M is a number of PET detector rings and $x_i$ and $x_{i+1}$ correspond to positions of a PET detector ring positioned at a first dashed line 726 and to a PET detector ring positioned at a second dashed line 727, respectively, but may correspond to any adjacent PET detector rings 701 arranged along the aFOV 709 of the patient 710. In satisfying the above-described equation, a distance 712 between PET detector rings 701 may be determined such that, when the PET detector rings 701 are in the second position, an AUC is equal between each "gap" between the PET detector rings 701.

It can be appreciated that exemplary implementations of the methods described herein, as in FIG. 6A through FIG. 7B, are non-limiting and merely reflect possible realizations of the present disclosure. For instance, though attenuation counts and attenuation mask size were considered with reference to FIG. 6A and FIG. 6B and FIG. 7A and FIG. 7B, respectively, it can be imagined that other parameters, including those with and without radiation parameters, may be considered and applied. For instance, the attenuation data may be statistically-focused attenuation counts data, wherein y=f(n) describes a sum, a median, a maximum, or a power of sum, among others, of (1) events occurring across GRDs within a single detector ring or (2) events occurring across a predefined axial range of detector rings. In another instance, the attenuation data may be attenuation intensity data and the attenuation metric may be based on a statistical metric of the attenuation intensity data. In this way, the statistical metric may be a sum, a median, a maximum and a power of sum, among others.

Figure 8A:
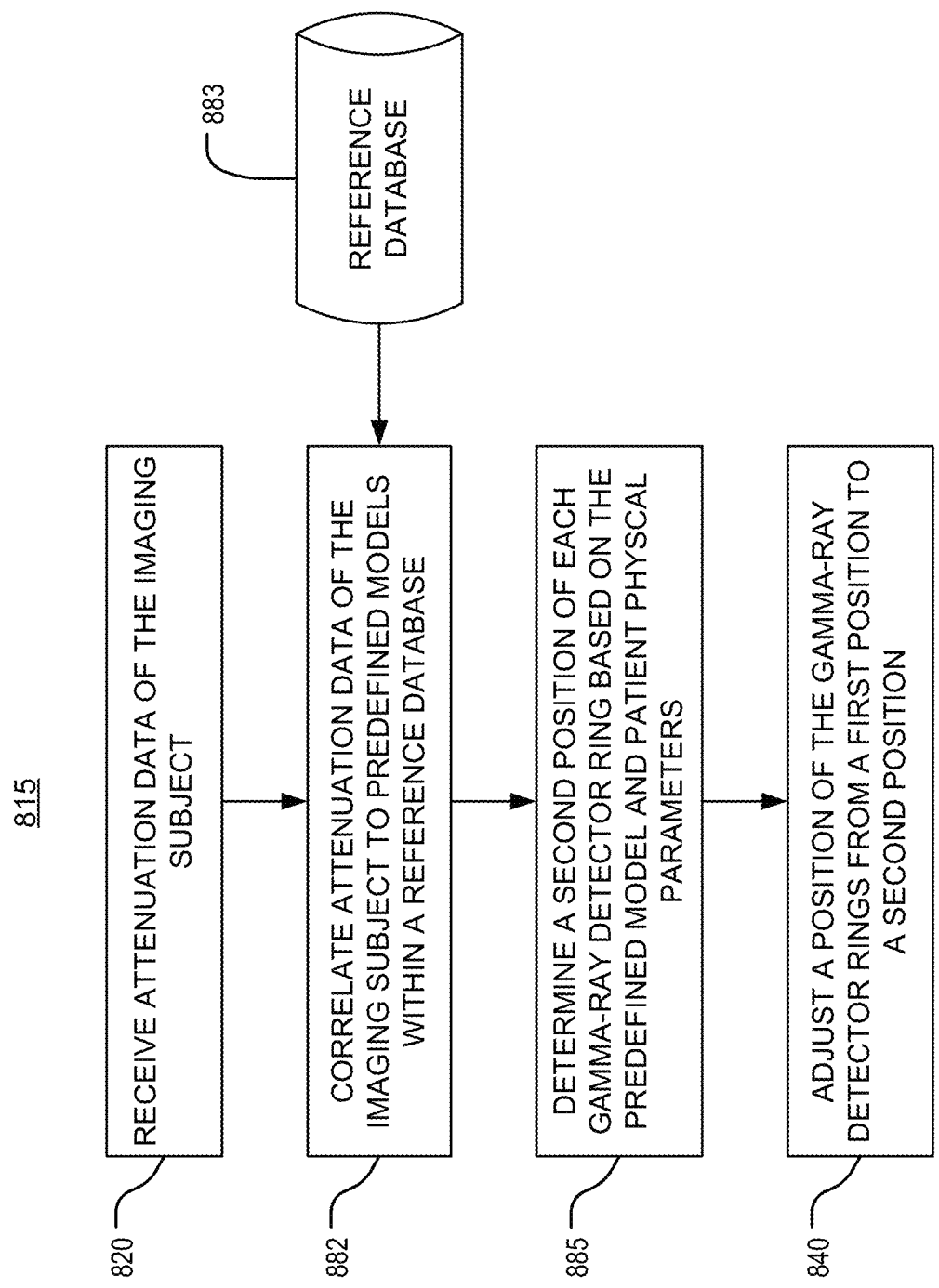
FIG. 8A is a flow diagram of a method of an adaptive axial field of view PET scanner, according to an exemplary embodiment of the present disclosure.

According to an embodiment, and with reference to FIG. 8A, method 815 describes an exemplary embodiment of the present disclosure. Generally, the method 815 relies on data from a CT scan of a patient to be imaged in order to define PET detector ring positions relative to the patient and an axial length of the CT scanner. In addition, the method 815 relies on a comparison of the acquired data from the CT scan with a plurality of reference data from a reference database to identify highly-correlated reference data, the highly-correlated reference data being associated with a predefined model that may be used for distribution of the PET detector rings along an axial length of the aaFOV PET scanner. In this way, based on the CT scan of the patient and the predefined model, the PET detector rings may be moved from a first position to a second position in order to provide improved imaging capabilities in a specific region of interest.

In particular, beginning at step 820 of method 815, attenuation data of a patient may be received. In an example, the attenuation data may be attenuation count data from each transaxial slice of a CT scan of the patient. The attenuation count data may define, for each transaxial slice of the CT scan of the patient, an amount of energy that is absorbed by a specific region of a patient along an axial length of the patient.

At step 882 of method 815, the acquired attenuation data may be compared with reference attenuation data stored within a reference database 883. The reference attenuation data may be data from previous iterations of PET scans and may be associated with acceptable distributions of PET detector rings. The previous iterations of PET scans may be associated with the same patient or with another patient having similar characteristics. In this way, the reference attenuation data corresponds to a predefined model defining an acceptable distribution (i.e., second positions) of PET detector rings. The comparison at step 882 of method 815 may be a correlation between the acquired attenuation data and the reference attenuation data stored within the reference database 883.

Upon identification of maximally-correlated reference attenuation data at step 882 of method 815, a predefined model associated therewith may be used at step 885 of method 815 in order to determine second positions of each PET detector ring. Determining the second positions of each PET detector ring includes application of the predefined model in view of specific patient information. For instance, the predefined model may include considerations for patient age, patient gender, patient weight, patient height (as it relates to aFOV), and the like. Moreover, by providing such information to the predefined model, the method is able to automatically generate second positions that are patient specific and demand minimal computational burden.

At step 840 of method 815, the second positions automatically determined at step 885 of method 815 can be used to adjust the PET detector rings from their first positions.

Appreciating, from FIG. 8A, that the second positions of the PET detector rings may be based upon a predefined model associated with attenuation data, it can be imagined that the predefined model may be associated with certain relevant patient profiles. For instance, a typical patient being evaluated for a lung issue may require an increased concentration of PET detector rings in the upper torso and, extrapolating this idea, predefined models may be designed to consider diagnostic applications in dictating second positions of PET detector rings. In another instance, excepting a diagnostic application, patient factors such as gender, weight, and medical conditions may be generally associated with specific predefined models. For example, the patient may be diabetic and, when compared with other diabetic patients, may benefit from a concentration of PET detector rings in the region of the lower extremities.

Figure 8B:
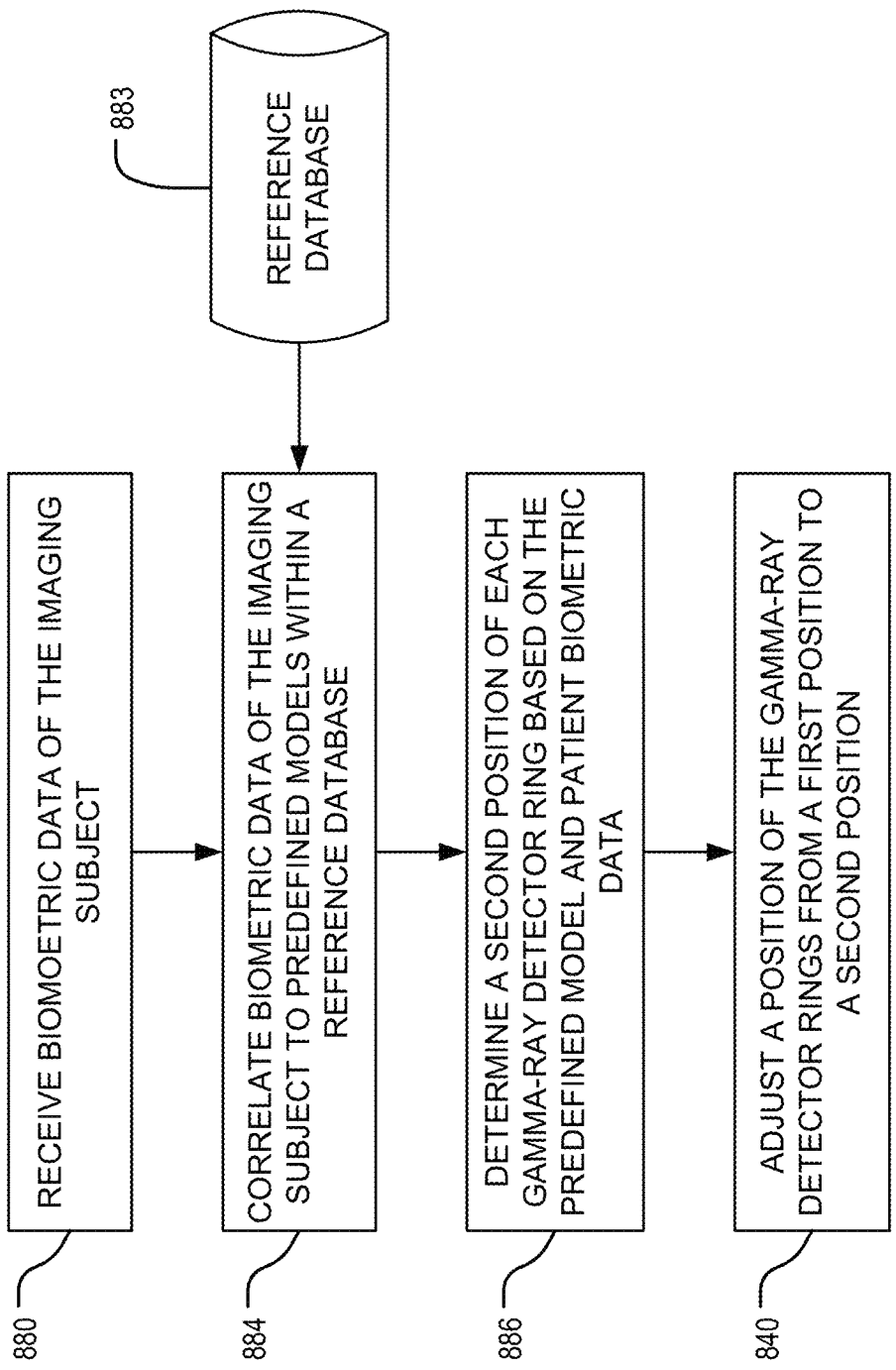
FIG. 8B is a flow diagram of a method of an adaptive axial field of view PET scanner, according to an exemplary embodiment of the present disclosure.

Further, and with reference now to FIG. 8B, method 815 describes an exemplary embodiment of the present disclosure, wherein radiation data is not required. Generally, the method 815 relies on physical patient data, or patient biometric data, which may include weight, height, and gender, among others, of a patient to be imaged in order to define PET detector ring positions relative to the patient and an axial length of the CT scanner. In addition, the method 815 relies on a comparison of the acquired patient biometric data with a plurality of reference biometric data from a reference database to identify highly-correlated reference biometric data, the highly-correlated reference biometric data being associated with a predefined model that may be used for distribution of the PET detector rings along an axial length of the aaFOV PET scanner. In this way, based on the patient biometric data and the predefined model, the PET detector rings may be moved to a second position in order to provide improved imaging capabilities in a specific region of interest.

In particular, beginning at step 880 of method 815, biometric data of a patient may be received. In an example, the biometric data of the patient may include height, weight, gender, body-mass index, shape, and ethnicity, among others.

At step 884 of method 815, the acquired biometric data may be compared with reference biometric data stored within a reference database 883. The reference biometric data may be biometric data from previous patients and may be associated with acceptable distributions of PET detector rings. The acceptable distributions of PET detector rings, therefore, are associated with another patient or group of patients having similar biometric characteristics. In this way, the reference biometric data corresponds to a predefined model defining an acceptable distribution (i.e., second positions) of PET detector rings. The comparison at step 884 of method 815 may be a correlation between the acquired biometric data and the reference biometric data stored within the reference database 883.

Upon identification of maximally-correlated reference biometric data at step 884 of method 815, a predefined model associated therewith may be used at step 886 of method 815 in order to determine second positions of each PET detector ring. Determining the second positions of each PET detector ring includes application of the predefined model and allows for automatic generation of second positions that are patient specific.

At step 840 of method 815, the second positions automatically determined at step 886 of method 815 can be used to adjust the PET detector rings from their first positions.

In addition to calculating attenuation metrics and/or identifying predefined models that may be applied to a given patient, second positions of PET detector rings may be identified in accordance with a focal point indicated by a radiologists or other clinician. With reference to FIG. 9A and FIG. 9B, a patient is illustrated in an aFOV PET scanner having an aFOV 909 capturing a length of the patient 910. As in FIG. 9A, PET detector rings 901 may be arranged at equal distances, or equal PET detector ring spacing 912, such that the length of the patient 910 is equally captured. Of course, methods described above with reference to FIG. 4 through FIG. 7B may be applied, but a clinician may also choose to manually define a specific region of interest about which the second position of the PET detector rings 901 will be determined. For instance, as in FIG. 9B, the clinician may indicate a focal point 955 as the region of interest of the patient 940 and a position about which the second positions of the PET detector rings 901 should be determined. In this way, PET detector rings 901 may be arranged at a first PET detector spacing 912' and a second PET detector spacing 912", for example, relative to the focal point 955 such that a single PET detector ring 901 is located at the focal point 955 and a distance between adjacent PET detector rings 901 increases with distance away from the focal point 955. In an embodiment, the first PET detector ring spacing 912' may be mirrored on the opposite side of the focal point 955, and this mirroring effect may be continued for the spacing of each subsequent and adjacent PET detector ring 901.

Figure 9C:
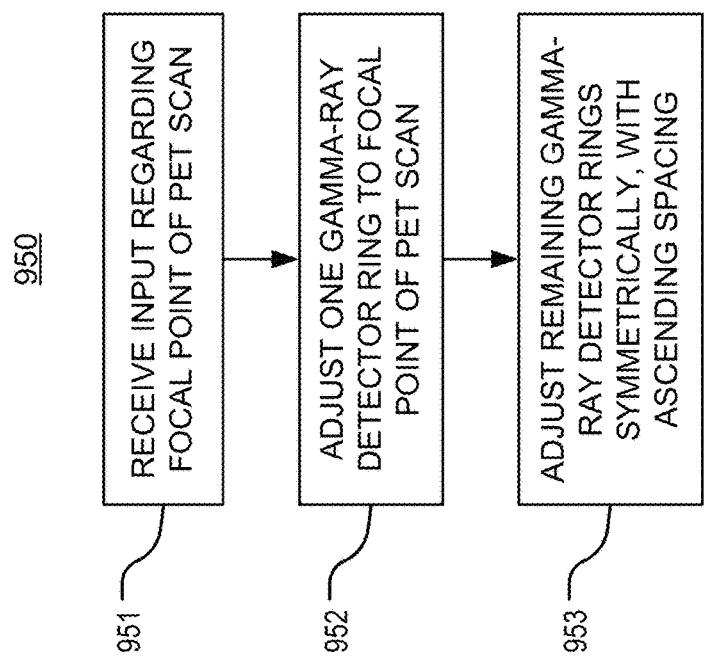
FIG. 9C is a flow diagram of a method of an adaptive axial field of view PET scanner, according to an exemplary embodiment of the present disclosure.

The method described with reference to the illustrations of FIG. 9A and FIG. 9B will now be described with reference to the flow diagram of FIG. 9C.

At step 951 of method 950, an input regarding a focal point of a PET scan may be received. The input may be provided by a clinician in accordance with a region of interest of the patient. In an embodiment, the focal point may be provided in context of an aFOV of the patient, wherein the aFOV of the patient is dictated by, in part, a length, or height, of the patient. At step 952 of method 950, a first PET detector ring may be adjusted to the focal point, as its second position. At step 953 of method 950, the remaining PET detector rings may be adjusted to second positions based on the PET detector ring positioned at the focal point. For instance, a first PET detector ring positioned away from the focal point may be positioned at a minimum PET detector ring spacing. A second PET detector ring positioned away from the focal point may be positioned at an increasing distance or spacing from the first PET detector ring. This trend may continue and may be mirrored on an opposite side of the focal point until the specified aFOV is met.

Figure 10:
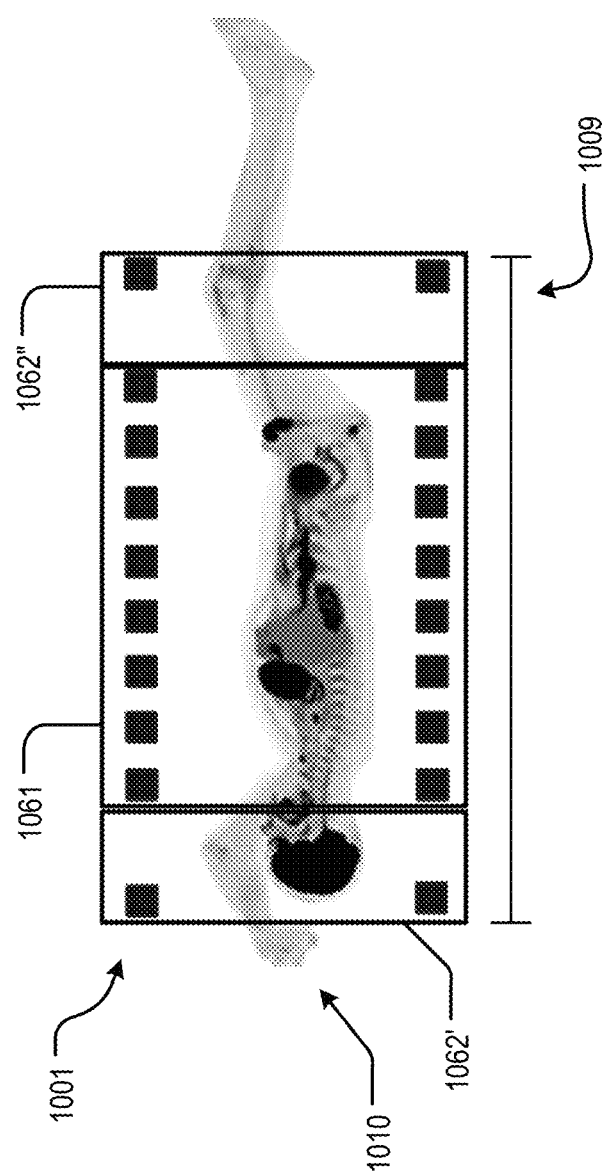
FIG. 10 is an illustration of a supplementary method of an adaptive axial field of view PET scanner, according to an exemplary embodiment of the present disclosure.

According to an embodiment, an aFOV of a patient, and an identified region of interest thereof, may only include a torso of a patient, as in FIG. 10. Accordingly, a central region of interest 1061 of the patient 1010 may include a majority of available PET detector rings 1001 of an aaFOV PET scanner. The second positions of the PET detector rings 1001 within the central region of interest 1061 may be based, in part, on the methods described throughout the above description of the present disclosure.

In an embodiment, and in order to more accurately recreate an image of the central region of interest 1061, one or more PET detector rings 1001 may be adjusted to second positions within a peripheral region of interest 1062', 1062" of the patient. The peripheral region of interest 1062' at the cranial end of the patient 1010 and the peripheral region of interest 1062" toward the lower extremities of the patient 1010 may be included within an aFOV 1009 of the patient 1010. In this way, annihilation events occurring within the central region of interest 1061 that generate gamma-rays traveling outside the central region of interest 1061 may be captured. Additionally, the generated gamma-rays traveling outside the central region of interest 1061 may be coincident or may be scattered, the scattered gamma-rays thereby being captured by the PET detector rings within the peripheral region of interest 1062', and 1062". In this way, incident events at PET detector rings within the peripheral regions of interest 1062', 1062" may be used to estimate scatter within the central region of interest 1061 and improve image reconstruction.

It can be appreciated that, while presented as a single PET detector ring within each peripheral region of interest 1062', 1062" in FIG. 10, the number of PET detector rings outside the central region of interest 1061 may vary according to a specific application and anticipated scatter events. Moreover, the distance occupied by the PET detector rings of the peripheral region of interest 1062', 1062" may vary according to a specific application anticipated scatter events.

Figure 11:
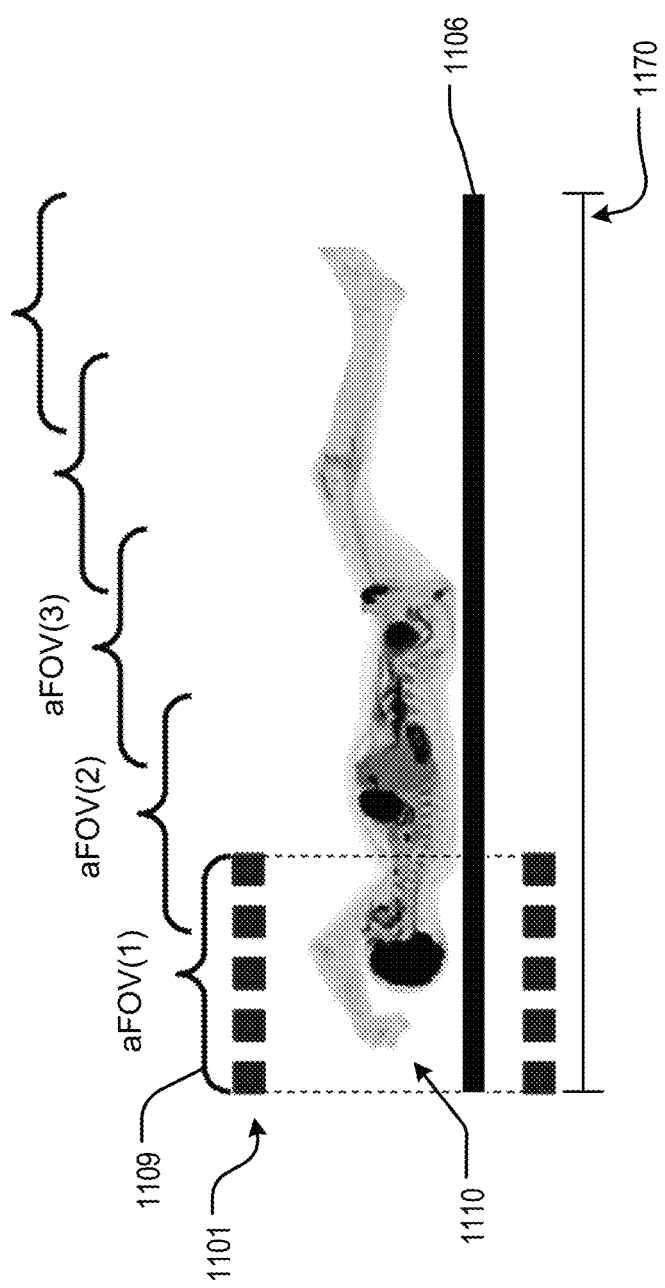
FIG. 11 is an illustration of a method of an axial field of view PET scanner, according to an exemplary embodiment of the present disclosure.

With reference now to FIG. 11, the aaFOV PET scanner of the present disclosure may be implemented in the absence of prior imaging data. In an example, in this case, the aaFOV PET scanner may provide a whole-body PET scan by implementing a series of PET scans having shorter aFOV.

In an embodiment, a patient 1110 that may benefit from total-body PET may be arranged on a table 1106 of the aaFOV PET scanner. The table 1106 of a PET scanner may be surrounded by PET detector rings 1101. The PET scanner may have a fixed maximal FOV 1170. Additionally, the table 1106 upon which the patient 1110 is arranged may be fixed. In order to acquire data of the patient 1110, an aFOV 1109 of the PET detector rings 1101 may be adjusted and a series of step-and-shoot images may be acquired. For instance, an aFOV(1), aFOV(2), aFOV(3), and the like, may comprise PET detector rings 1101 having minimal PET detector ring spacing. The PET detector rings 1101 may be moved together between each aFOV, or image acquisition sequence. In an embodiment, and in order to collect a whole-body PET scan, the PET detector rings 1101 may be adjusted through the fixed maximal FOV 1170 of the aaFOV PET scanner, from aFOV(1) at a head of the patient 1110 to a final aFOV near feet of the patient 1110. In order to ensure image collation, an overlap of a predetermined number of PET detector rings 1101 may be implemented. In an example, the predetermined number of PET detector rings 1101 identified for overlap is two.

It may be further appreciated that a new method of PET reconstruction using the aaFOV PET scanner can be used given the adjustment of the PET detector rings from the first position to the second position, and so on, allowing scans with different geometries and reconstruction FOVs with variable size and location. That is, the aaFOV PET scanner changes configuration and does not have a fixed, one-system geometry, so any look-up tables used for reconstruction may be changed. Furthermore, since the aaFOV PET scanner and the PET detector rings therein may change during the scan, not all LORs may have the same acquisition time and the same start and end time. Thus, a reconstruction method capable of adapting to the aaFOV PET scanner changes is desired.

In an embodiment, as the positions of the crystals or detectors change over time, location information for the crystals may not simply be read from a crystal index; the physical locations of the crystals also need to be determined for each time point. In order to enable this determination, during data acquisition the physical locations of the crystals may be saved for each crystal. For example, when data acquisition occurs, the physical locations of the crystals can be indexed with each pair detection.

In an embodiment, a global coordinate system covering the largest possible reconstructable FOV for the aaFOV PET scanner and all detectors may be determined. In all scans, locations of image voxels and detectors may be determined according to the global coordinates. Although the aaFOV PET scanner can change geometry, there is still a limit to the change for the aaFOV PET scanner and based on a largest possible geometry or shape, global coordinates can be provided to cover all possible subsets of geometries.

In an embodiment, an image coordinate system may be used that is agnostic to changes in the aaFOV PET scanner. Before the data acquisition, based on the FOV and voxel sizes, a constant initial image space may be specified in (x,y,z) coordinates and kept fixed. All the crystals may then be positioned according to those image coordinates. The crystal coordinates can be specified according to the image coordinate, which means no matter where the crystals move, the location of the crystal can always be pinpointed or located based on the image coordinates.

In some PET scanners without aaFOV, all the crystals may begin and end detecting simultaneously, meaning all the crystals may start the scan at the same time and the scan may have a single, global scan duration. In the aaFOV PET scanner, crystal positions may change during data acquisition, and thus each LOR may start acquiring data at a different time and for a different duration. Therefore, the scan start time and duration may no longer be kept for the whole scan, but rather, for each individual LOR. That is, the timing information for each LOR may not be globally applied.

In an embodiment, the spatial location, starting time (st) at that location, and ending time (et) at that location may be saved. The crystals may have multiple positions during the whole acquisition, and st and et may be saved separately for each position. For example, assume two crystals form a LOR connecting two points corresponding to the two crystal locations. Notably, now that the crystals may be adjusted, the corresponding position of the LOR may now be specified when referring to the LOR. Thus, that means that for the same crystal pair, the position of the LOR may now be different.

For example, assume two crystals form the LOR connecting $(x_1, y_1, z_1)$ and $(x_2, y_2, z_2)$. The crystals may be positioned at $(x_1, y_1, z_1)$ between $st_1$ and $et_1$, and positioned at $(x_2, y_2, z_2)$ between $st_2$ and $et_2$. The paired coincidence in this LOR may be assigned with a starting time max $\{st_1, st_2\}$, and scan duration min$\{et_1, et_2\}$−max $\{st_1, st_2\}$. Note that if min$\{et_1, et_2\}$<max$\{st_1, st_2\}$, there isn't coincidence. For each paired event, the following information may be stored: i) indices of the two crystals recording the detection event, ii) locations of the two crystals recording the detection event, iii) start time for the LOR connecting the two crystals, and iv) scan duration for the LOR connecting the two crystals. For example, for an aaFOV PET scanner having 100 crystals, the index may be from 1 to 100. The index for the crystal may be specified because the crystal may have intrinsic physical properties, such as crystal normalization values. Even if the crystal changes position, the crystal normalization is still related to the index of the crystal.

In an embodiment, the starting and ending times may be grouped into subsets. For example, the starting and ending times may be grouped by a phase or state of the scan. During an acquisition, there may be several phases, such as a first phase where all the crystals are in a first predetermined arrangement and a second phase where all the crystals are in a second predetermined arrangement, wherein each phase may have corresponding start and end times. That is, for example, the first phase may have detected events with all the same start and end times in a first subset where the crystals are spread far apart, and the second phase may have detected events with all the same start and end times in a second subset where the crystals are grouped closer together at a predetermined focal point. Each subset may similarly have a corresponding LOR different from one another. The grouping of the acquisition data may be especially advantageous for aiding in accurate reconstruction of data obtained from using the aaFOV PET scanner.

In an embodiment, a sinogram-based iterative reconstruction method may be used. The estimated image $\bar{f}$ may be updated according to $$\bar{f}_j^{k+1} = \frac{\bar{f}_j^k}{\sum_i H_{ij}} \sum_i H_{ij} \frac{g_i/(\eta_i^{Decay}\eta_i^{Duration}\eta_i^{xtalEff}\eta_i^{detgeom}\eta_i^{atten})}{\sum_{n=0}^{N-1} H_{in}\bar{f}_n^k + \frac{sc_i + r_i}{\eta_i^{detgeom}\eta_i^{atten}}}$$

In an embodiment, a list mode-based reconstruction method may be used. The estimated image $\bar{f}$ may be updated according to $$\bar{f}_j^{k+1} = \frac{\bar{f}_j^k}{\sum_i H_{ij}} \sum_b^B H_{i \ni b, j} \frac{1/(\eta_{i \ni b}^{Decay}\eta_{i \ni b}^{Duration}\eta_{i \ni b}^{xtalEff}\eta_{i \ni b}^{detgeom}\eta_{i \ni b}^{atten})}{\sum_{n=0}^{N-1} H_{i \ni b, n}\bar{f}_n^k + \frac{sc_{i \ni b} + r_{i \ni b}}{\eta_{i \ni b}^{detgeom}\eta_{i \ni b}^{atten}}}$$

where, for both reconstruction methods, $H_{ij}$ is the system matrix, and N is the total number of voxels in the image. Further, i represents the ith LOR connecting the predetermined locations of crystals in the PET rings, and may be from different crystals since crystals can move during acquisition. Further, j represents the jth voxel in the image domain, B is the total number of events, i∋b denotes the ith LOR at which the bth event is detected, and $sc_i$ and $r_i$ are scatter and random correction factors. Further, $\eta_i^{Decay}$ is the decay correction factor, $\eta_i^{Duration}$ is the duration correction factor, $\eta_i^{xtalFff}$ is the crystal efficiency normalization, $\eta_i^{detgeom}$ is the geometry normalization, $\eta_i^{atten}$ is the attenuation correction factor.

In both sinogram and list mode-based reconstruction for the aaFOV PET scanner, it may be most efficient to generate the system matrix on-the-fly, and system matrix components $H_{ij}$ may be generated using either the global coordinates or the image coordinates. Here, because the aaFOV PET scanner crystals may be either predefined for each acquisition or changed during acquisition, the system matrix for the scanner may not be pre-saved or pre-generated. Since the system matrix is based on the image voxel and detector coordinates at a given time, $H_{ij}$ represents the weight connecting voxel j and LOR i based on their locations at time t. The weights can be determined by various methods, such as ray tracing, area simulated volume, etc.

For the decay/duration correction, when the system matrix is only based on the voxel and detector coordinates at a given time, the decay/duration correction for each LOR or event may be performed. The scan start/duration time for each LOR may be different, therefore the decay correction for each LOR should be different:

$$\eta_i^{Decay}=(e^{-\lambda s_i}-e^{-\lambda(s_i+t_i)})/\lambda t_i$$

where $s_i$, $t_i$ are the starting and duration times for LOR i, and $\lambda$ is the decay constant. Similarly, the duration correction of each LOR should be $\eta_i^{Duration}=t_i$.

In an embodiment, crystal efficiencies may not change as crystals move to different locations. Therefore, the most compact FOV size possible may be used for crystal efficiency measurement. Then, the measured crystal efficiencies may be used for any geometry.

In an embodiment, since the configuration of the aaFOV PET scanner is not fixed, there may not be a single geometric normalization for all possible geometries of the aaFOV PET scanner. To overcome this difficulty, geometry normalization may be calculated for the largest FOV by one or multiple measurements. There may be limited possible LORs for use in geometry normalization. During image reconstructions, all possible LORs may be from linear interpolation of the LORs used in the geometry normalization. Additionally or alternatively, projectors that properly account for geometric effects may be used so that there is no need for geometric normalization. Additionally or alternatively, the geometry normalization may be accomplished by assuming a plurality of virtual crystals and then the geometry normalization factors may be calculated for each virtual location. Then, if one of the actual crystals is in that location, then the corresponding the geometry normalization for that virtual location may be used. In other words, the geometry normalization for all possible positions that can be occupied by the crystals may be calculated because geometry is changing. Notably, although an infinite number of virtual locations may exist, a finite or discrete number of positions may be set for any aaFOV PET scanner. For the infinite or continuous set of positions, geometry normalization may be measured for a fixed number of virtual crystal positions and then interpolated to the desired continuous position.

In an embodiment, for attenuation correction, a CT image of the same size with the PET image and a PET attenuation map may be used for attenuation correction. The attenuation factor for each LOR may be calculated using $$\alpha_i = e^{-\Sigma_j H_{ij} \mu_j}$$

where $\mu_j$ is the attenuation coefficient index for voxel i.

In an embodiment, for scatter estimation, the estimated scatter for a fixed LOR will remain constant for the scan for that LOR. In tail fitting during scatter correction, the measurement sinograms should be corrected by decay and duration corrections before fitting with estimated scatter sinograms in the tail regions. The tail fitting is based on the measured sinogram, but due to the scattered motion or scattered movements, the tail of the measured sinogram may be different from different positions. In this case, for the tail fitting, the measured sinogram may be re-scaled based on the duration, or the duration information may be incorporated into the scatter estimation. For example, two crystals for a LOR and based on the estimated image a scatter may be estimated roughly as the scatter shape for this LOR. However, the true scaling of the scatter may be difficult to estimate. To account for this, random and scatter events (also known as randoms and scatters, respectively) detected towards an outside or periphery of a patient or phantom can be analyzed. Prompt events (also known as prompts, or detection events measured within a coincidence window) may then have the randoms subtracted from the prompts to yield the scatters. This profile for the LOR outside the patient outline or periphery with the scatters may be considered the tail region. The estimated scatters may be matched as best as possible with the measured scatters, wherein the measured scatters may be defined as the prompts minus the delayed events (also known as delays) in the tail region.

For randoms correction, due to the noise in the measured sinograms both for the primary timing window and delayed timing windows, measured events in the delayed timing window may be smoothed before random correction. Usually when the delay events are used to estimate the randoms, smoothing may be performed because the direct delayed event is quite noisy. Thus, smoothing in the sinogram domain may be desired, which may then be used to smooth with the random corrections. However, because each LOR may have a different acquisition time, a smooth on the sinogram may not be directly applied. For example, assume a first LOR with a short acquisition time and a neighboring second LOR with a longer acquisition time. If both are simply smoothed, a bias may be introduced.

To this end, in an embodiment, a first smoothing method may apply different decay and duration correction factors before smoothing. In an embodiment, a second smoothing method may calculate a randoms ratio for each LOR based on delay window events and primary window events. A new sinogram may be formed where each element is the randoms ratio for each LOR comprising fixed crystal locations. Then, this sinogram of randoms ratios may be smoothed and these smoothed entries may be used in the reconstruction for each LOR.

In an embodiment, a time-varying system matrix may be used. In both sinogram and list mode reconstruction, the system matrix may be generated on-the-fly, as there will be different starting/duration time for each LOR. The decay/duration factors can be included in the system matrix. Then $$W_{ij} = H_{ij}\eta_i^{Decay}\eta_i^{Duration} = H_{ij}(e^{-\lambda s_i} - e^{-\lambda(s_i+t_i)})/\lambda$$

where $H_{ij}$ is the weight for the LOR connecting voxel j and LOR i at time t. This may be advantageous for modeling the imaging statistics. In this case, the reconstruction may therefore be $$\bar{f}_j^{k+1} = \frac{\bar{f}_j^k}{\sum_i W_{ij}} \sum_i W_{ij} \frac{g_i/(\eta_i^{xtalEff}\eta_i^{detgeom}\eta_i^{atten})}{\sum_{n=0}^{N-1} W_{in}\bar{f}_n^k + \frac{sc_i + r_i}{\eta_i^{detgeom}\eta_i^{atten}}}, \text{ and}$$

$$\bar{f}_j^{k+1} = \frac{\bar{f}_j^k}{\sum_i W_{ij}} \sum_b^B W_{i\ni b,j} \frac{1/(\eta_{i\ni b}^{xtalEff}\eta_{i\ni b}^{detgeom}\eta_{i\ni b}^{atten})}{\sum_{n=0}^{N-1} W_{i\ni b,n}\bar{f}_n^k + \frac{sc_{i\ni b} + r_{i\ni b}}{\eta_{i\ni b}^{detgeom}\eta_{i\ni b}^{atten}}}.$$

Notably, the estimated scatter and randoms may include time indices.

In an example, for two LORs, one with a very low detection count and the other with a very high detection count, the high count LOR will have better imaging information and the low count LOR will have worse imaging information, which means having high noise. However, knowing both LORs are from the same scan subject, directly applying the duration correction on the two LORs will result in multiplying or enhancing the LOR with a shorter acquisition and low count. More noise will then be introduced when a same weight is applied during reconstruction to the low count LOR. If the timing factor is included or factored into the forward projection, the LOR with the short acquisition and lower count will have a smaller weight and lower impact on the resultant image. Notably, the normalization is preserved. Thus, there is no bias and less weight is used on the LOR with the noisier events.

Figure 12:
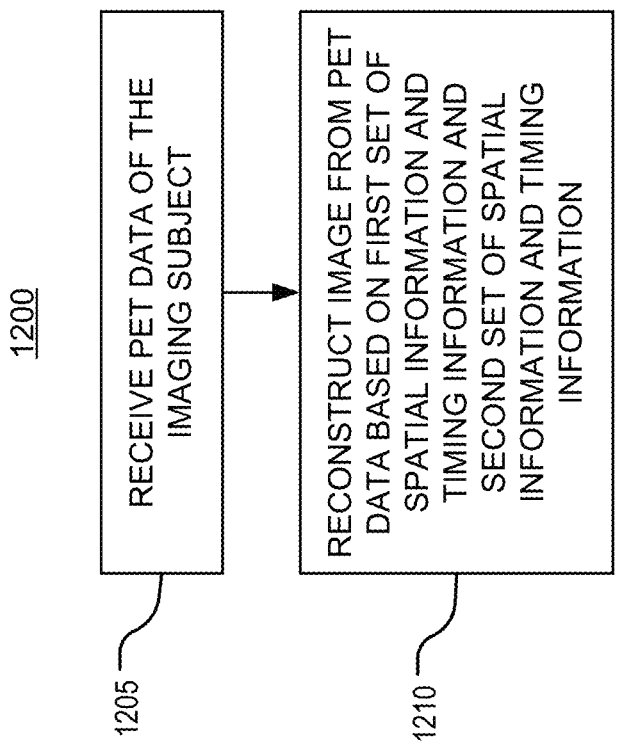
FIG. 12 is a flow diagram of a method of reconstructing an image using the adaptive axial field of view PET scanner.

The methods described previously are summarized with reference to method 1200 of FIG. 12. In step 1205, the PET data of the imaging subject is received. The PET data, again, can include a first set of spatial information and timing information corresponding to a data acquisition time for the crystals and detector rings in a first axial position along the axial length of the aaFOV PET scanner and a second set of spatial information and timing information corresponding to a data acquisition time for the crystals and detector rings in a second axial position along the axial length of the aaFOV PET scanner. For example, the first set of spatial information and timing information can occur during a first scan phase where the crystals and detector rings are in the first axial position. Then, the crystals and detector rings can translate to the second axial position, and the second set of spatial information and timing information can occur during this second scan phase with the new positions and timings.

In step 1210, the PET data can be used to reconstruct an image, the PET data including the first set of spatial information and timing information corresponding to a data acquisition time for the crystals and detector rings in the first axial position along the axial length of the aaFOV PET scanner and the second set of spatial information and timing information corresponding to a data acquisition time for the crystals and detector rings in the second axial position along the axial length of the aaFOV PET scanner. The reconstruction method can be a sinogram-based iterative reconstruction. The reconstruction method can be a list mode-based iterative reconstruction.

Obviously, numerous modifications and variations are possible in light of the above teachings. It is therefore to be understood that within the scope of the appended claims, the invention may be practiced otherwise than as specifically described herein.

Embodiments of the present disclosure may also be as set forth in the following parentheticals.

(1) A positron emission tomography (PET) scanner, comprising a plurality of gamma-ray detector rings that form a bore through which an imaging subject is translated, a length of the bore defining an axial length of the PET scanner, the plurality of gamma-ray detector rings being movable along the axial length, the plurality of gamma-ray detector rings each including gamma-ray detector modules therein, and processing circuitry configured to receive PET data associated with a plurality of transaxial slices of the imaging subject, the PET data including a first set of spatial information and timing information corresponding to a first data acquisition period for the gamma-ray detector modules in a first axial position along the axial length and a second set of spatial information and timing information corresponding to a second data acquisition period for the gamma-ray detector modules in a second axial position along the axial length, and reconstruct a PET image based on the received PET data, including the first set of spatial information and timing information and the second set of spatial information and timing information.

(2) The positron emission tomography scanner according to (1), wherein for each line of response (LOR) and for each position of the first axial position and the second axial position: the corresponding spatial information includes respective positions of two crystals defining of the LOR, and the corresponding timing information includes a start time and end time of data acquisition for each of the two crystals.

(3) The positron emission tomography scanner according to either (1) or (2), wherein the gamma-ray detector modules are disposed in at least two axial positions during a scan of the imaging subject, and the start time and the end time are saved separately for each position of the gamma-ray detector modules.

(4) The positron emission tomography scanner according to any one of (1) to (3), wherein the at least two axial positions are different for any particular gamma-ray detector module of the plurality of gamma-ray detectors.

(5) The positron emission tomography scanner according to any one of (1) to (4), wherein the processing circuitry is further configured to reconstruct the PET image using a sinogram-based iterative reconstruction process based on each line of response (LOR) connecting corresponding locations within two of the gamma-ray detector modules detecting an annihilation event having a different start time and end time corresponding to each of the at least two axial positions, the sinogram-based iterative reconstruction process being further based on a geometry normalization factor, a scatter correction factor, and a random correction factor.

(6) The positron emission tomography scanner according to any one of (1) to (5), wherein the processing circuitry is further configured to reconstruct the PET image data using a list mode-based iterative reconstruction process based on each line of response (LOR) having a different start time and end time corresponding to each of the at least two axial positions, the list mode-based iterative reconstruction process being further based on a system matrix, a total number of voxels in the image, a total number of detected events, a decay correction factor, a duration correction factor, a crystal efficiency normalization factor, a geometry normalization factor, an attenuation correction factor, a scatter correction factor, and a random correction factor.

(7) The positron emission tomography scanner according to any one of (1) to (6), wherein the scatter correction factor is determined by applying a decay correction and a duration correction before applying a tail fitting to the scatter correction.

(8) The positron emission tomography scanner according to any one of (1) to (7), wherein the random correction factor is determined by applying a decay correction and a duration correction before applying a smoothing to the random correction.

(9) The positron emission tomography scanner according to any one of (1) to (8), wherein the random correction factor is determined by determining a randoms ratio for said each LOR based on delay and primary window events, generating a new sinogram based on the determined randoms ratio, and smoothing the sinogram based on the randoms ratio.

(10) The positron emission tomography scanner according to any one of (1) to (9), wherein the geometry normalization factor is determined by measuring a geometry normalization at a largest field of view of the PET scanner with the gamma-ray detector modules disposed at predetermined first positions and interpolating a geometry normalization for the gamma-ray detector modules at predetermined second positions between the predetermined first positions.

(11) The positron emission tomography scanner according to any one of (1) to (10), wherein the processing circuitry is further configured to generate and update a system matrix during the scan of the imaging subject, and the processing circuitry is further configured to reconstruct the PET image using the system matrix including decay correction and the duration correction for each line of response (LOR).

(12) A method of a positron emission tomography scanner, comprising receiving, by processing circuitry, PET data associated with a plurality of transaxial slices of an imaging subject, the imaging subject being translated through a bore defined by a plurality of gamma-ray detector rings positioned along a length of the bore defining an axial length of the PET scanner, the plurality of gamma-ray detector rings each including gamma-ray detector modules therein, the PET data including a first set of spatial information and timing information corresponding to a first data acquisition period for the gamma-ray detector modules in a first axial position along the axial length and a second set of spatial information and timing information corresponding to a second data acquisition period for the gamma-ray detector modules in a second axial position along the axial length; and reconstructing, by the processing circuitry, a PET image based on the first set of spatial information and timing information and the second set of spatial information and timing information.

(13) The method according to (12), wherein for each line of response (LOR) and for each position of the first axial position and the second axial position: the corresponding spatial information includes respective positions of two crystals defining of the LOR, and the corresponding timing information includes a start time and end time of data acquisition for each of the two crystals.

(14) The method according to either (12) or (13), wherein the gamma-ray detector modules are disposed in at least two axial positions a scan of the imaging subject, and the start time and the end time are saved separately for each position of the gamma-ray detector modules.

(15) The method according to any one of (12) to (14), wherein the at least two axial positions are different for any particular gamma-ray detector module of the plurality of gamma-ray detectors.

(16) The method according to any one of (12) to (15), wherein the step of reconstructing the PET image further comprises using a sinogram-based iterative reconstruction process based on each LOR having a different start time and end time corresponding to each of the at least two axial positions, the sinogram-based iterative reconstruction process being further based on a system matrix, a total number of voxels in the image, a decay correction factor, a duration correction factor, a crystal efficiency normalization factor, a geometry normalization factor, an attenuation correction factor, a scatter correction factor, and a random correction factor.

(17) The method according to any one of (12) to (16), wherein the step of reconstructing the PET image further comprises using a list mode-based iterative reconstruction process based on each LOR having a different start time and end time corresponding to each of the at least two axial positions, the list mode-based iterative reconstruction process being further based on a system matrix, a total number of voxels in the image, a total number of detected events, a decay correction factor, a duration correction factor, a crystal efficiency normalization factor, a geometry normalization factor, an attenuation correction factor, a scatter correction factor, and a random correction factor.

(18) The method according to any one of (12) to (17), further comprising generating and updating a system matrix during the scan of the imaging subject, and reconstructing the PET image using the system matrix including decay correction and the duration correction for each line of response (LOR).

(19) A non-transitory computer-readable storage medium storing computer-readable instructions that, when executed by a computer, cause the computer to perform a method of a positron emission tomography (PET) scanner, comprising receiving, by processing circuitry, PET data associated with a plurality of transaxial slices of an imaging subject, the imaging subject being translated through a bore defined by a plurality of gamma-ray detector rings positioned along a length of the bore defining an axial length of the PET scanner, the plurality of gamma-ray detector rings including gamma-ray detector modules therein, the PET data including a first set of spatial information and timing information corresponding to a first data acquisition period for the gamma-ray detector modules in a first axial position along the axial length and a second set of spatial information and timing information corresponding to a second data acquisition period for the gamma-ray detector modules in a second axial position along the axial length; and reconstructing, by the processing circuitry, a PET image based on the first set of spatial information and timing information and the second set of spatial information and timing information.

(20) The non-transitory computer-readable storage medium according to (19), wherein for each line of response (LOR) and for each position of the first axial position and the second axial position: the corresponding spatial information includes respective positions of two crystals defining of the LOR, and the corresponding timing information includes a start time and end time of data acquisition for each of the two crystals.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

The invention claimed is:

1. A positron emission tomography (PET) scanner, comprising:
 a plurality of gamma-ray detector rings that form a bore through which an imaging subject is translated, a length of the bore defining an axial length of the PET scanner, the plurality of gamma-ray detector rings being movable along the axial length, the plurality of gamma-ray detector rings each including gamma-ray detector modules therein, and
 processing circuitry configured to
  receive PET data associated with a plurality of transaxial slices of the imaging subject, the PET data including a first set of spatial information and timing information corresponding to a first data acquisition period for the gamma-ray detector modules in a first axial position along the axial length and a second set of spatial information and timing information corresponding to a second data acquisition period for the gamma-ray detector modules in a second axial position along the axial length, and
  reconstruct a PET image based on the received PET data, including the first set of spatial information and timing information and the second set of spatial information and timing information, wherein for each line of response (LOR) and for each position of the first axial position and the second axial position:
   the corresponding spatial information includes respective positions of two crystals defining the LOR, and
   the corresponding timing information includes a start time and an end time of data acquisition for each of the two crystals,
wherein the gamma-ray detector modules are disposed in at least two axial positions during a scan of the imaging subject,
wherein the start time and the end time are saved separately for each position of the gamma-ray detector modules, and
wherein the processing circuitry is further configured to reconstruct the PET image using a sinogram-based iterative reconstruction process based on each line of response (LOR) connecting corresponding locations within two of the gamma-ray detector modules detecting an annihilation event having a different start time and end time corresponding to each of the at least two axial positions, the sinogram-based iterative reconstruction process being further based on a geometry normalization factor, a scatter correction factor, and a random correction factor.

2. The positron emission tomography scanner according to claim 1, wherein the at least two axial positions are different for any particular gamma-ray detector module of the plurality of gamma-ray detectors.

3. A positron emission tomography scanner, comprising:
a plurality of gamma-ray detector rings that form a bore through which an imaging subject is translated, a length of the bore defining an axial length of the PET scanner, the plurality of gamma-ray detector rings being movable along the axial length, the plurality of gamma-ray detector rings each including gamma-ray detector modules therein, and
processing circuitry configured to
   receive PET data associated with a plurality of transaxial slices of the imaging subject, the PET data including a first set of spatial information and timing information corresponding to a first data acquisition period for the gamma-ray detector modules in a first axial position along the axial length and a second set of spatial information and timing information corresponding to a second data acquisition period for the gamma-ray detector modules in a second axial position along the axial length, and
   reconstruct a PET image based on the received PET data, including the first set of spatial information and timing information and the second set of spatial information and timing information,
wherein for each line of response (LOR) and for each position of the first axial position and the second axial position:
   the corresponding spatial information includes respective positions of two crystals defining the LOR, and
   the corresponding timing information includes a start time and an end time of data acquisition for each of the two crystals,
wherein the gamma-ray detector modules are disposed in at least two axial positions during a scan of the imaging subject,
wherein the start time and the end time are saved separately for each position of the gamma-ray detector modules, and
wherein the processing circuitry is further configured to reconstruct the PET image data using a list mode-based iterative reconstruction process based on each line of response (LOR) having a different start time and end time corresponding to each of the at least two axial positions, the list mode-based iterative reconstruction process being further based on a system matrix, a total number of voxels in the image, a total number of detected events, a decay correction factor, a duration correction factor, a crystal efficiency normalization factor, a geometry normalization factor, an attenuation correction factor, a scatter correction factor, and a random correction factor.

4. The positron emission tomography scanner according to claim 1, wherein the scatter correction factor is determined by applying a decay correction and a duration correction before applying a tail fitting to the scatter correction.

5. The positron emission tomography scanner according to claim 1, wherein the random correction factor is determined by applying a decay correction and a duration correction before applying a smoothing to the random correction.

6. The positron emission tomography scanner according to claim 1, wherein the random correction factor is determined by determining a randoms ratio for said each LOR based on delay and primary window events, generating a new sinogram based on the determined randoms ratio, and smoothing the sinogram based on the randoms ratio.

7. The positron emission tomography scanner according to claim 1, wherein the geometry normalization factor is determined by measuring a geometry normalization at a largest field of view of the PET scanner with the gamma-ray detector modules disposed at predetermined first positions and interpolating a geometry normalization for the gamma-ray detector modules at predetermined second positions between the predetermined first positions.

8. A positron emission tomography scanner, comprising:
a plurality of gamma-ray detector rings that form a bore through which an imaging subject is translated, a length of the bore defining an axial length of the PET scanner, the plurality of gamma-ray detector rings being movable along the axial length, the plurality of gamma-ray detector rings each including gamma-ray detector modules therein, and
processing circuitry configured to
   receive PET data associated with a plurality of transaxial slices of the imaging subject, the PET data including a first set of spatial information and timing information corresponding to a first data acquisition period for the gamma-ray detector modules in a first axial position along the axial length and a second set of spatial information and timing information corresponding to a second data acquisition period for the gamma-ray detector modules in a second axial position along the axial length, and
   reconstruct a PET image based on the received PET data, including the first set of spatial information and timing information and the second set of spatial information and timing information,
wherein for each line of response (LOR) and for each position of the first axial position and the second axial position:
   the corresponding spatial information includes respective positions of two crystals defining the LOR, and
   the corresponding timing information includes a start time and an end time of data acquisition for each of the two crystals, wherein the gamma-ray detector modules are disposed in at least two axial positions during a scan of the imaging subject, wherein the start time and the end time are saved separately for each position of the gamma-ray detector modules, and the processing circuitry is further configured to generate and update a system matrix during the scan of the imaging subject, and the processing circuitry is further configured to reconstruct the PET image using the system matrix including decay correction and duration correction for each line of response (LOR).

9. A method of a positron emission tomography (PET) scanner, comprising:

receiving, by processing circuitry, PET data associated with a plurality of transaxial slices of an imaging subject, the imaging subject being translated through a bore defined by a plurality of gamma-ray detector rings positioned along a length of the bore defining an axial length of the PET scanner, the plurality of gamma-ray detector rings each including gamma-ray detector modules therein, the PET data including a first set of spatial information and timing information corresponding to a first data acquisition period for the gamma-ray detector modules in a first axial position along the axial length and a second set of spatial information and timing information corresponding to a second data acquisition period for the gamma-ray detector modules in a second axial position along the axial length; and reconstructing, by the processing circuitry, a PET image based on the first set of spatial information and timing information and the second set of spatial information and timing information, wherein for each line of response (LOR) and for each position of the first axial position and the second axial position:

the corresponding spatial information includes respective positions of two crystals defining the LOR, and the corresponding timing information includes a start time and an end time of data acquisition for each of the two crystals, wherein the gamma-ray detector modules are disposed in at least two axial positions during a scan of the imaging subject, wherein the start time and the end time are saved separately for each position of the gamma-ray detector modules, and wherein the processing circuitry is further configured to reconstruct the PET image using a sinogram-based iterative reconstruction process based on each line of response (LOR) connecting corresponding locations within two of the gamma-ray detector modules detecting an annihilation event having a different start time and end time corresponding to each of the at least two axial positions, the sinogram-based iterative reconstruction process being further based on a geometry normalization factor, a scatter correction factor, and a random correction factor.

10. The method according to claim 9, wherein the at least two axial positions are different for any particular gamma-ray detector module of the plurality of gamma-ray detectors.

11. A method of a positron emission tomography (PET) scanner, comprising:

receiving, by processing circuitry, PET data associated with a plurality of transaxial slices of an imaging subject, the imaging subject being translated through a bore defined by a plurality of gamma-ray detector rings positioned along a length of the bore defining an axial length of the PET scanner, the plurality of gamma-ray detector rings each including gamma-ray detector modules therein, the PET data including a first set of spatial information and timing information corresponding to a first data acquisition period for the gamma-ray detector modules in a first axial position along the axial length and a second set of spatial information and timing information corresponding to a second data acquisition period for the gamma-ray detector modules in a second axial position along the axial length; and reconstructing, by the processing circuitry, a PET image based on the first set of spatial information and timing information and the second set of spatial information and timing information, wherein for each line of response (LOR) and for each position of the first axial position and the second axial position:

the corresponding spatial information includes respective positions of two crystals defining the LOR, and the corresponding timing information includes a start time and an end time of data acquisition for each of the two crystals, wherein the gamma-ray detector modules are disposed in at least two axial positions a scan of the imaging subject, wherein the start time and the end time are saved separately for each position of the gamma-ray detector modules, and wherein the step of reconstructing the PET image further comprises using a list mode-based iterative reconstruction process based on each LOR having a different start time and end time corresponding to each of the at least two axial positions, the list mode-based iterative reconstruction process being further based on a system matrix, a total number of voxels in the image, a total number of detected events, a decay correction factor, a duration correction factor, a crystal efficiency normalization factor, a geometry normalization factor, an attenuation correction factor, a scatter correction factor, and a random correction factor.

12. A method of a positron emission tomography (PET) scanner, comprising:

receiving, by processing circuitry, PET data associated with a plurality of transaxial slices of an imaging subject, the imaging subject being translated through a bore defined by a plurality of gamma-ray detector rings positioned along a length of the bore defining an axial length of the PET scanner, the plurality of gamma-ray detector rings each including gamma-ray detector modules therein, the PET data including a first set of spatial information and timing information corresponding to a first data acquisition period for the gamma-ray detector modules in a first axial position along the axial length and a second set of spatial information and timing information corresponding to a second data acquisition period for the gamma-ray detector modules in a second axial position along the axial length, wherein for each line of response (LOR) and for each position of the first axial position and the second axial position: the corresponding spatial information includes respective positions of two crystals defining of the LOR, and the corresponding timing information includes a start time and end time of data acquisition for each of the two crystals, wherein the gamma-ray detector modules are disposed in at least two axial positions a scan of the imaging subject, and the start time and the end time are saved separately for each position of the gamma-ray detector modules;

generating and updating a system matrix during the scan of the imaging subject; and reconstructing, by the processing circuitry, a PET image based on the first set of spatial information and timing information and the second set of spatial information and timing information, wherein the PET image is reconstructed using the system matrix including decay correction and duration correction for each line of response (LOR).

* * * * *